(12) United States Patent
Steller et al.

(10) Patent No.: US 6,235,524 B1
(45) Date of Patent: May 22, 2001

(54) COMPOSITIONS AND METHODS FOR SCREENING AGENTS THAT INHIBIT MAPK MEDIATED ANTI-APOPTOTIC SIGNALS

(75) Inventors: Hermann Steller, Sherborn; Julie Agapite, Cambridge; Kimberly McCall, Chestnut Hill; Andreas Bergmann, Cambridge, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/431,573

(22) Filed: Oct. 29, 1999

Related U.S. Application Data

(60) Provisional application No. 60/106,108, filed on Oct. 29, 1998.

(51) Int. Cl.[7] .......................... C07H 21/04; C12N 15/00; C12N 15/09; C12N 15/63; C12N 15/70
(52) U.S. Cl. .................. 435/320.1; 536/23.1; 435/320.1; 435/325; 435/440; 530/350
(58) Field of Search ................... 536/23.1, 23.5; 435/320.1, 325, 440; 530/350

(56) References Cited

PUBLICATIONS

Grether et al, Genes and Development, 1995, 9: 1694–1708.*

* cited by examiner

*Primary Examiner*—Scott D. Priebe
*Assistant Examiner*—Peter Paras, Jr.
(74) *Attorney, Agent, or Firm*—Medlen & Carroll, LLP

(57) ABSTRACT

Nucleic acid sequences and corresponding translated products of novel mutant forms of the *Drosophila hid* gene are described. Such sequences and products are useful in screening methods for identifying and testing antagonists of Hid phosphorylation, in particular, compositions modifying MAPK phosphorylation of Hid.

3 Claims, 14 Drawing Sheets

(5 of 14 Drawing Sheet(s) Filed in Color)

atggccgtgcccttttatttgcccgagggcggcgccgatgacgtagcgtcgagttcatcggcctcggcaactcctc
ccccacaaccaccactccctcgagcgcatcctcgtcctcgtctcctcggcgtgtcctcggcctcctccgctcctcgg
cctcatcttcgtcatccgcatcgtcgacggcgcagcagcgccgcaatcgccgaacaccacctcgtcggcc
acgcagacgccgatgcagtctccactgcccaccgaccaagtgctatacgccctctacgagtgggtcaggatgtaccagag
ccagcagagtgcccgcaaatcttccagtatccgccgccaagcccttgcaattcactgccgcgatgtgttctttc
cgcacggccatccgaatccgaactcgcacccatccggcacccccgaaccagcgtgagcttctcctccggcgaggag
tacaacttcttccggcagcagcagccgcaacacatccgtcatatccggcagcagtcggccatcaacaccgagccaccgca
gtcagcgccgatgactacctactacgcggctgagcgcacacagctacccggccaccacccctcacgtcgacctccacgcgtcctccctttcg
gaatgggcggtacctactacgcggctgagcgcacacagctacccggccaccacccctcacgtcgacctccacgcgtcctccctttcg
gcggccttcggctgcacggccaccccacagccccttcacgtcgacctccacgcgttatcggccagtggcgccaa
gatgcctgcagcgcagccagtcggatgcggccagacgcaagcgattgacctcgacgcggcgagatgagcgagtacc
agagcgatcatgaggcacttggacgagttggcgatcgctacgacaacttacggccggagcgtctgcaggag
ttcaatgaccgcatcccgcgtggtacatcccaagcggagagcggtgccatccatgccacatccagcagcaatatccagtctgccatac
cgacagccagtccggtggtacatcccaagcggagagcggtgccatccatgccacatcagtcagcagcgacaggtggagc
gagaacgacaaaggcgaaggcgagaagagaaaccacagagcttcacttggccaactgttgtgaccgtttcgttttg
gccatgggctgtggcttctttgcggcgatga

FIG. 9 atggccgtgcccttttatttgccgagggcgccgatgacgtagcgtcgagttcatcggagcctcggcaactcctc
ccccacaaccaccactccctcgagcgcatcctcgtccgtcctcctccggcgtcctcggcctccggcctcctcgg
cctcatcttcgtcatccgcatcgtcggacggccagcagccgcctcgcaatcgccgaacaccaccacctgtcggcc
acgcagacgccgatgcagtctccactgccaccagtgctatacgccctctacgagtgggtcaggatgtaccagag
ccagcagagtgccccgcaaatcttccagtatccgccgccaagcccctcttgcaatttcactggcgatgtgttcttc
cgcacggccatccgaatccgaactcgaatccccgaaccagcgtgagcttcctccggcgaggag
tacaacttcttccggcagcagccgcaaccacatccgtcatcagcaccgcagcaatgccaccgca
gtcagcgccgatgcactgcagccacagctacccgcagcagtcgcacacaccattccgctccttcg
gaatgggcgtacctacgccgcgctacacgccactccgaacacgccagtgccgcacctccagctcatcg
gcggcctttcggctggcacgccaccggccacccccttcacgtcgaccgccgttatcggcgcagtggccgccaa
gatgcgcctgcagcgccgagcaggccagtggcggccaagcgattgacctcgacgggcgaggatgagcgagtacc
agagcgatcatgaggcactgggacgagtttggcgatcgctacgacaacttacggccggccgggagcgtcgcaggag
ttcaatgacgcatcccgccccgaagaagagagctccaatagccactcgagcagcaataatccagtctgccatac
cgacagccagtccggtggtacatcccaagcggagagcggtgccatccatggccacatcagtcagcagcagtggagc
gagaacgacaaaggcgaaggcgagaagaaccacagagcttcactggccaactgttgtgaccgtttttcgttttg
gccatgggctgtggctttctttgcggcgcgatga

```
atggccgtgcccttttatttgcccgagggcggcgatgacgtagcgtcgagttcatccggagcctcggcaactcctc
ccccaaccaccactccctcgagccatcctcgtcctccctcgtgtcctccggcgtcctcggcctccgcctcctcgg
cctcatcttcgtcatccgcgatcgtcgagcggccagcagccgccgccaatcgccgaacaccaccacctcgtcgcc
acgcagacgccgatgcagtctccactgccaccgaccaagtgctatacgccctctacgagtggtcaggatgtaccagag
ccagcagagtgccccgcaaatcttccagtatccgcccgccagccctcttgcaattcactggcgatgtgttcttc
cgcacggccatccgaactcgaatcccatccgcgggccccgaaccagcgtgagcttctcctccggcgaggag
tacaacttcttccggcagcagccgcaacagccgtcatatccgcgccatcagccgcagcaatgccaccgca
gtcagcgccgatgactggtacctactacgccgctacacagccgcaccacccgcttcacgtcgacctccagctcatcg
gaatggggcggtacctactacgccgctacacgccgccaccccccttcacgtcgacgtcgacccctcccc... 
```

FIG. 11

MAVPFYLPEGGADDVASSSSGASGNSSPHNHPLPSSASSSVSSSGVSSASASSASSSSASSDGASSAASQSPNTTTSSA

TQTPMQSPLPTDQVLYALYEWVRMYQSQQSAPQIFQYPPPSPSCNFTGGDVFFPHGHPNPNSNPHPRAPRTSVSFSSGEE

YNFFRQQQPQQPHPSYPAPSAPQPMPPQSAPPMHCSHSYPQQSAHMMPHHSAPFGMGGTYYAGYTPPPTPNTASAGTSSSS

AAFGWHGHPHAPFTSTSTPLSAPVAPKMRLQRSQSDAARRKRLTSTGEDEREYQSDHEATWDEFGDRYDNFTAGRERLQE

FNGRIPPRKKKSSNSHSSSSNNPVCHTDSQSGGTSQAESGAIHGHISQQRQVEREROKAKAEKKKPQSFTWPTVVTVFVL

AMGCGFFAAR

FIG. 12

MAVPFYLPEGGADDVASSSSGASGNSSPHNHPLPSSASSSVSSSGVSSASASASSSSASSSDGASSAASQSPNTTTSSA
TQTPMQSPLPTDQVLYALYEWVRMYQSQQSAPQIFQYPPPAPSCNFTGGDVFFPHGHPNPNSNPHPRAPRTSVSFSSGEE
YNFFRQQQPQPHPSYPAPSAPQPMPPQSAPPMHCSHSYPQQSAHMMPHHSAPFGMGGTYYAGYTPPPAPNTASAGTSSSS
AAFGWHGHPHAPFTSTSTPLSAPVAPKMRLQRSQSDAARRKRLTSTGEDEREYQSDHEATWDEFGDRYDNFTAGRERLQE
FNGRIPPRKKKSSNSHSSSSNNPVCHTDSQSGGTSQAESGAIHGHISQQRQVERERQKAKAEKKKPQSFTWPTVVTVFVL
AMGCGFFAAR

COMPOSITIONS AND METHODS FOR SCREENING AGENTS THAT INHIBIT MAPK MEDIATED ANTI-APOPTOTIC SIGNALS

This application for a regular U.S. Utility Application claims priority to, and perfects the filing date of, Provisional U.S. Patent Application Ser. No. 60/106,108 filed on Oct. 29, 1998.

FIELD OF THE INVENTION

This invention generally relates to the nucleic acid sequences (and corresponding translated products) of novel mutant forms of the *Drosophila hid* gene and methods of identifying and sting antagonists of Hid phosphorylation, in particular, compositions modifying MAPK phosphorylation of Hid.

BACKGROUND OF THE INVENTION

Programmed cell death (PCD) is mediated by a process called apoptosis. Although the investigation of cell death is a relatively new field of study, it has become readily apparent that many disease states are manifested due to the aberrant control of programmed cell death. Recent evidence suggest that the failure of cells to undergo apoptotic cell death might be involved in the pathogenesis of a variety of human diseases including cancer, autoimmune diseases and viral infections. The understanding of survival pathways would be critical in disease states where excessive cell numbers, such as in various cancers, are the result of cell survival signals preventing cell death rater than the result of uncontrolled proliferation. It is known that a number of peptide factors including the neurotrophins, Insulin-like growth factor 1 (IGF-1), fibroblast growth factor (FGF), and epidermal growth factor (EGF) promote cell survival by suppressing the intrinsic cell death program. The growth factors listed above bind to and activate their respective receptor tyrosine kinases (RTK) at the cell surface which, in turn, stimulate the anti-apoptotic activity of the proto-oncogene ras. Ras controls the activity of a number of effector pathways, two of which result in activation of protein kinases known to mediate its anti-apoptotic effect: the mitogen activated protein kinase p42p44 (MAPK) of the ERK-type (extracellular signal-related kinase) via Raf and the Akt kinase via phosphoinositide 3-kinase (PIK-3). Mutational activation of ras oncogenes is associated with about 30% of all human tumors, potentially suppressing the ability of the body to remove the cancerous cell.

The product of the gene hid is responsible for inducing apoptosis in drosophila embryos as well as transfected insect and mammalian cells. When ectopically expressed, Hid induces apoptosis by activating a caspase protease pathway. In the absence of Hid function many cells that should die fail to do so. Unlike other cell death activating genes (e.g. reaper and grim), hid is expressed in many cells that are not destined to undergo apoptosis. This observation suggests that efficient post-translational survival mechanisms operate in these cells to protect them from Hid-induced apoptosis. Activation of the Ras/MAPK pathway in transfected cells has been shown to decrease or inhibit Hid-induced cell death.

The screening of potential therapeutics has been hindered by both a lack of understanding of the physiological basis of cell death and by a dearth of reagents specific for critical points in the cell death signaling pathways. Additionally, much work has focused on the delineation of the death-inducing pathway and reagents that may block it and not on pathways that confer survival signals. What is needed are reagents and methodologies that allow for the identification and testing of agonists and antagonists of cell survival pathways.

SUMMARY OF THE INVENTION

The present invention generally relates to compositions and methods of identifying and testing Hid pathway agonists and antagonists, and in particular, compositions modifying MAPK phosphorylation of Hid. In addition, the invention relates to methods to identify other members of the Hid signal pathway, methods to identify homologs of Hid which are native to other tissue or cell types and methods to generate reagents derived from the invention.

The present invention contemplates employing novel mutant forms of the wild-type *Drosophila hid* gene (SEQ ID NO:1) in these screening methods. In one embodiment, the present invention contemplates replacing nucleic acid of the *Drosophila hid* gene encoding phosphoacceptor residues with nucleic acid encoding non-phosphorylatable amino acids (e.g. alanine). In one embodiment, the present invention contemplates a composition comprising isolated and purified DNA having an oligonucleotide sequence selected from the group consisting of: $Hid^{Ala3}$ cDNA having the nucleotide sequence of SEQ ID NO:2; and $Hid^{Ala5}$ cDNA having the nucleotide sequence of SEQ ID NO:3. Such DNA may readily be inserted into expression constructs and the present invention contemplates such constructs as well as their use. The present invention also contemplates RNA transcribed from the above-indicated cDNAs as well as protein (typically purified protein) translated from this RNA. Moreover, the present invention contemplates antibodies produced from immunizing with this translated protein.

The present invention also contemplates transgenic animals comprising the above-indicated DNA (i.e. the "transgene") or portions thereof. In a particular embodiment, the transgenic animal of the present invention may be generated with the transgene contained in an inducible, tissue specific promotor.

The present invention also contemplates using the above-named compositions in screening assays. The present invention is not limited by the particular method of screening. In one embodiment, the present invention contemplates screening suspected compounds in a system utilizing transfected cell lines. In one embodiment, the cells may be transfected transiently. In another embodiment, the cells may be stably transfected. In yet another embodiment translation products of the invention may be used in a cell-free assay system. In yet another embodiment, antibodies generated to the translation products of the invention may be used in immunoprecipitation assays.

The present invention may also be used to identify new constituents of the Hid signaling pathway. In one embodiment, antibodies generated to translation products of the invention may be used in immunoprecipitation experiments to isolate novel Hid pathway constituents or natural mutations thereof. In another embodiment, the invention may be used to generate fusion proteins that could also be used to isolate novel Hid pathway constituents or natural mutations thereof. In yet another embodiment screens maybe conducted using the yeast two-hybrid system.

The present invention may also be used to identify new homologs of Hid or natural mutations thereof. The present invention contemplates screening for homologs using standard molecular procedures. In one embodiment screens are conducted using Northern and Southern blotting.

The present invention contemplates a method of screening a compound, said method comprising: a) providing in any order: i) a first group of cells comprising a recombinant expresssion vector, wherein said vector comprises at least a portion of the oligonucleotide sequence of SEQ ID NOS:2 or 3, ii) a second group of cells comprising a recombinant expression vector, wherein said vector comprises at least a portion of the wild-type Drosophila hid gene oligonucleotide sequence (SEQ ID NO:1), and iii) at least one compound suspected of having the ability to modulate MARK/ Hid pathway activity; b) contacting said first and second groups of cells with said compound; and c) detecting programmed cell death modulation effects of said compound.

The present invention contemplates another method of screening a compound where the compound exerts an apoptotic effect by causing the multimerization of the translated product of the invention. Multimerization of Hid may be required for its activation. Phosphorylation of Hid by MAPK may prevent said multimerization. It is believed that compounds that multimerize Hid can potentially activate nonphosphorlatable Hid thereby initiating apoptosis. Said method comprising a) providing in any order: i) a first group of cells comprising a first recombinant expression vector, wherein said first vector comprises at least a portion of the oligonucleotide sequence of SEQ ID NOS:2 or 3, ii) a second group of cells comprising a second recombinant expression vector, wherein said second vector comprises at least a portion of the wild-type Drosophila hid gene oligonucleotide sequence (SEQ ID NO:1), and iii) at least one compound suspected of having the ability to multimerize (i.e. capable of multimerizing) Hid; b) contacting said first and second groups of cells with said compound (i.e. in separate reactions); and c) detecting programmed cell death modulation effects of said compound.

The present invention also contemplates a method of screening for homologs, said method comprising: a) providing in any order: i) first nucleic acid comprising at least a portion of the sequence of SEQ ID NOS:2 or 3, ii) second nucleic acid comprising at least a portion of the sequence of SEQ ID NO:1; and iii) DNA libraries from cells or tissues suspected to comprise said homolog; and b) hybridizing said first or second nucleic acid with said DNA of said library under conditions such that said DNA suspected of coding for said homolog is detected.

The present invention also contemplates a method of screening for interactive peptides, said method comprising: a) providing in any order: i) a peptide comprsing at least a portion of the peptide sequence of SEQ ID NOS:4 or 5 (including but not limited to portions that are part of fusion proteins, i.e. proteins that contain another portion, such as a portion useful for protein purification) and b) an extract from source (e.g. cells or tissues) suspected of having said interactive peptides; and c) mixing said peptide with said extract under conditions such that said interactive peptide is detected.

The present invention contemplates another approach for screening for interactive peptides, said method comprising: a) providing in any order: i) antibodies reactive with (and usually specific for) at least a portion of a peptide having the sequence of SEQ ID NOS:4 or 5, and ii) an extract from a source (e.g. cells or tissues) suspected of having said interactive peptide(s); and b) mixing said antibody with said extract under conditions such that said interactive peptide is detected.

The file of this patent contains at least one drawing executed in color. Copies of this patent with color drawings are provided to the Patent and Trademark Office with payment of the necessary fee.

(A) Wild-type. (B) Eye ablation phenotype caused by one copy of the GMR-hid$^{10}$ transgene. Note the strong reduction in eye size in comparison to A. (C–E) Dominant suppression of the GMR-hid$^{10}$-induced eye phenotype by lof mutations in gap1$^{21-1s}$, spry$^{28-4s}$ and arg$^{7\Delta7}$. (F) Schematic drawing of the EGFR/Ras1/MAPK signaling pathway and the relative position of the inhibitory genes gap1, argos and sprouty. Arg and Spry are secreted polypeptides which inhibit EGFR activation. Gap1 promotes the GTPase-activity of Ras1. Abbreviations used: EGF (epidermal growth factor), Drk (downstream of receptor kinase), Sos(Son of sevenless), Dsor (downstream suppressor of raf), MAPK (mitogen activated protein kinase), MEK (MAPK-Erk kinase).

Figure 2:
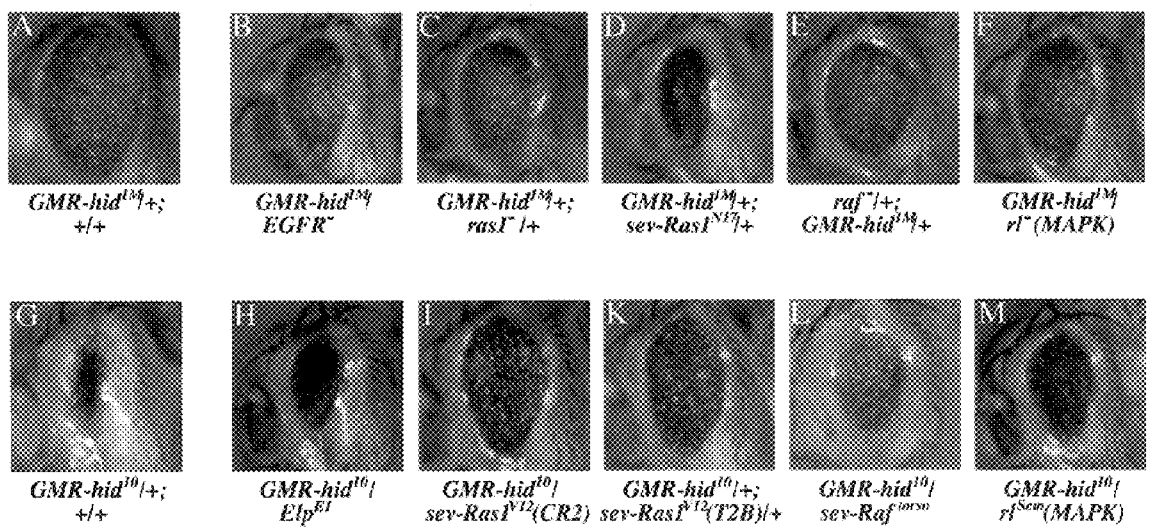

FIG. 2(A–M) shows genetic interaction of EGFR/Ras1/ MAPK pathway mutants with GMR-hid. The mild eye ablation phenotype of GMR-hid$^{1M}$ (A) was used to score for enhancement caused by lof mutants of EGFR (B), ras1 (C), raf (E) and rl/MAPK (F) or caused by the dominant negative sev-Ras1$^{N17}$ transgene (D). Note the smaller eyes in (B,C, D,E,F) compared to the unmodified GMR-hid$^{1M}$ eye. The sev-Ras1$^{N17}$ transgene behaves as the strongest enhancer (D). The eye phenotypes of heterozygous EGFR$^-$, ras1$^-$, raf$^-$ and rl$^-$/MAPK flies alone are phenotypically wild-type (data not shown). The dominant negative sev-Ras1$^{N17}$ allele alone produces a mild rough eye phenotype as the result from the loss of R7 cells (Karim et al. "Immediate-early baculovirus vectors for foreign gene expression in transformed or infected insect cells", Protein Expr. Punif 8:191–203, 1996); the eye size, however, is not affected by sev-Ras1$^{N17}$.

The strong eye ablation phenotype of GMR-hid$^{10}$ (G) was used to score for suppression caused by gof mutants and transgenes of EGFR (Elp$^{E1}$,H), sev-Ras1$^{V12}$ (I, K), sev-Raf$^{torso}$ (L) and rl$^{Sem}$/MAPK. The strongest suppression is seen with the two sev-Ras1$^{V12}$ transgenes used (CR2 and T2B). The genotypes of flies shown are indicated below each panel.

Figure 3:
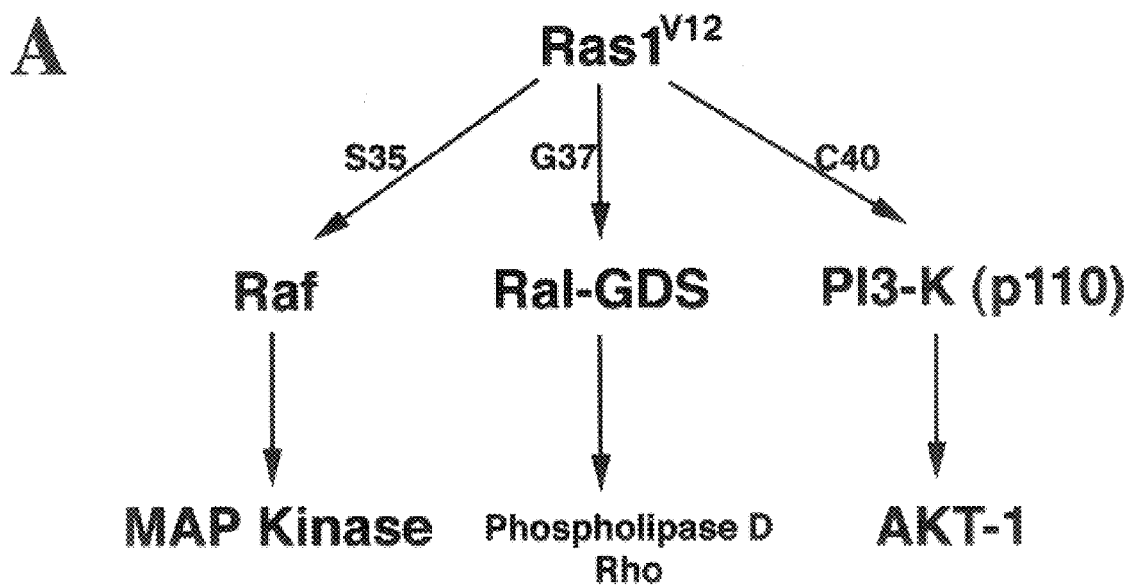
Figure 3:
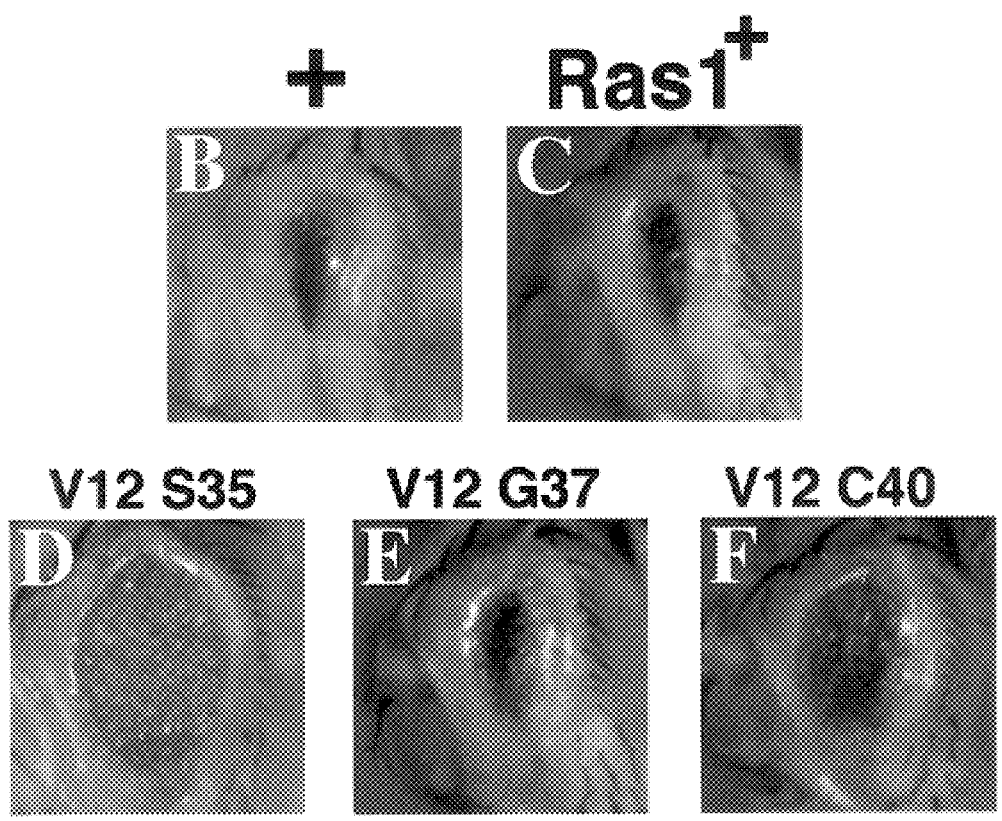

FIG. 3(A–F) shows the Raf/MAPK effector branch of Ras1 is the major pathway for suppression of GMR-hid. (A) Schematic outline of the downstream effector pathways of Ras1 and of the effector loop mutations in Ras1 leading specifically to activation of only one effector branch. For instance, Ras1$^{V12S35}$ interacts with Raf, but not with Ral-GDS and PI3-K; Ras1$^{V12G37}$ only interacts with Ral-GDS; Ras1$^{V12C40}$ only interacts with the p110 subunit of PI3-K. (B) Eye ablation phenotype caused by GMR-hid$^{10}$ sev-GAL4. (C) Wild-type Ras1 does not modify the GMR-hid$^{10}$ eye phenotype. (D) Activation of the Raf/MAPK pathway by Ras1$^{V12S35}$ results in strong suppression of GMR-hid$^{10}$. The quantitatively stronger suppression seen in this experiment compared to FIG. 2M is due to stronger expression of Ras1$^{V12S35}$ caused by the GAL4/UAS system. (E) The Ral.GDS effector pathway fails to suppress GMR-hid$^{10}$. (F)

Activation of the PI3-K/Akt pathway by Ras1$^{V12C40}$ results in moderate suppression of GMR-hid$^{10}$. The genotypes are: (B) GMR-hid$^{10}$ sev-GAL4/+; (C) GMR-hid$^{10}$ sev-GAL4/UAS-Ras1$^+$; (D) GMR-hid$^{10}$ sev-GAL4/UAS-Ras1$^{V12S35}$; (E) GMR-hid$^{10}$ sev-GAL4/UAS-Ras1$^{V12G37}$; (F) GMR-hid$^{10}$ sev-GAL4/UAS-Ras1$^{V12C40}$.

Figure 4:
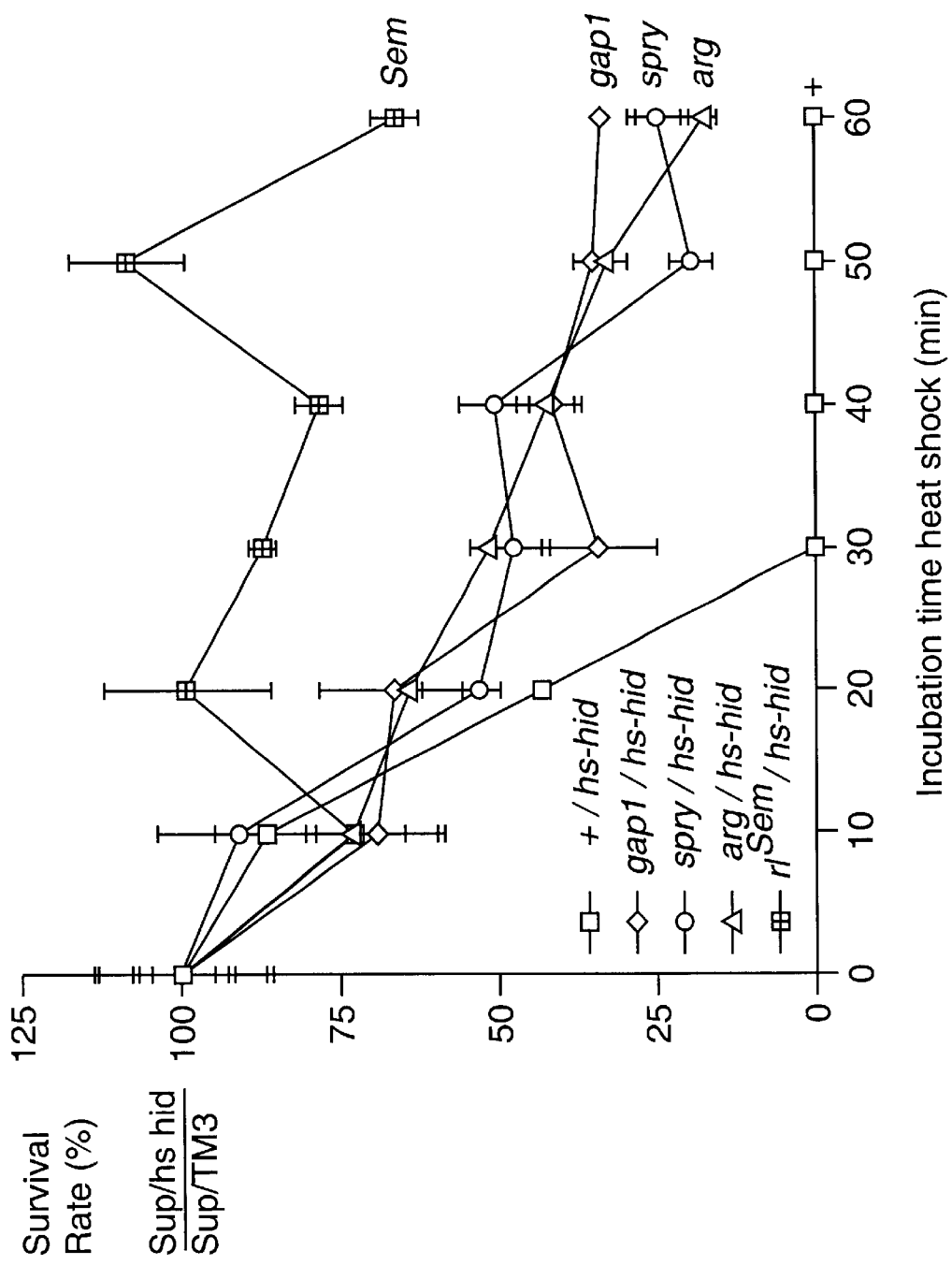

FIG. 4 shows dominant suppression of hs-hid-induced lethality. Heat shock induction of hid via a hs-hid transgene during first instar larvae causes strong organismal lethality (Grether et al. "The head involution defective gene of *Drosophila melanogaster* functions in programmed cell death", *Genes Dev.* 9: 1694–1708, 1995). After 30 min of heat shock, only 2% of the hs-hid animals survive compared to control (non hs-hid) animals. Lof mutations in gap1, spry and arg protect against hs-hid-induced lethality, such that about 20–40% of Sup/hs-hid animals survive even a 60 min heat shock at 37° C. The gof mutation rl$^{Sem}$/MAPK has the strongest survival activity against hs-hid-induced lethality. Approximately 70% of rl$^{Sem}$; hs-hid animals survive a 60 min heat shock at 37° C. The genotype of flies analyzed in this assay are +/hs-hid, gap1$^{2I-1s}$/hs-hid, spry$^{28-4s}$/hs-hid, arg$^{IA7}$/hs-hid and rl$^{Sem}$/+; hs-hid/+. The results shown represent the average of three independently performed experiments.

Figure 5:
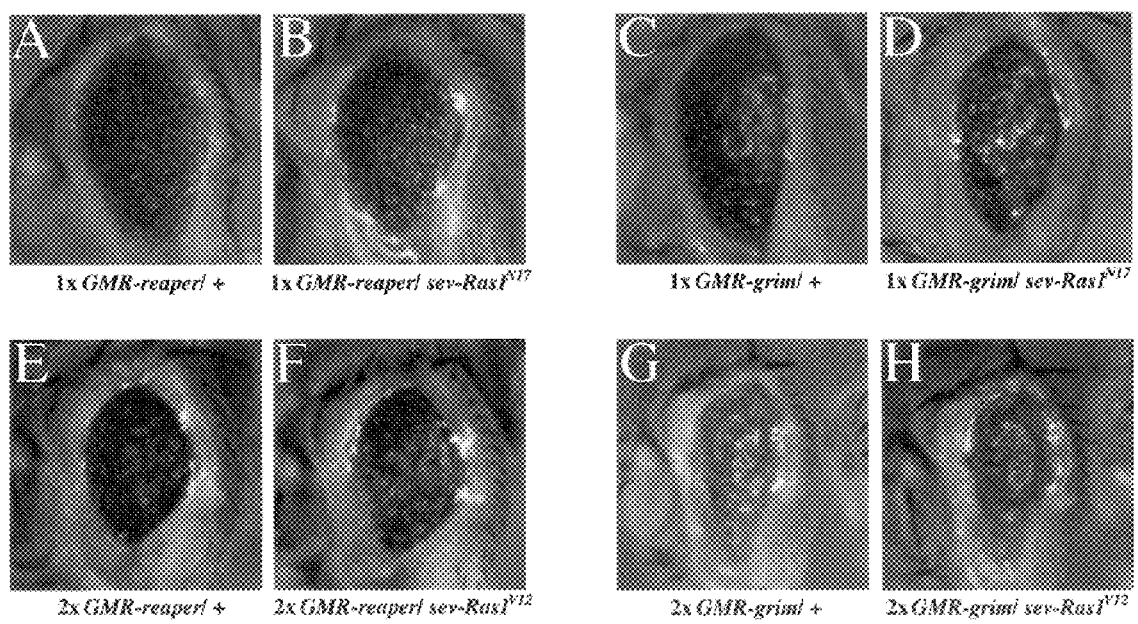

FIG. 5(A–H) shows that GMR-reaper- and GMR-grim-induced eye phenotypes are not affected by EGFR/Ras1/MAPK signaling. The mild eye ablation phenotypes caused by one copy of GMR-reaper (A) and GMR-grim (C) were used to score for an enhancement by the dominant-negative Ras1 allele sev-Ras1$^{N17}$ (B and D). Stronger eye ablation phenotypes were produced by two copies of either GMR-reaper (E) or GMR-grim (G), and were used to test for suppression by the gof Ras1 allele sev-Ras1$^{V12}$ (F and H). Both Ras1 transgenes, sev-Ras1$^{N17}$ and sev-Ras1$^{V12}$, do not or only weakly modify either the GMR-rpr- or GMR-grim-induced eye phenotypes. These Ras1 transgenes show striking effects on GMR-hid-induced apoptosis (see FIG. 2D and 2I). Other EGFR/Ras1/MAPK pathway mutants also fail to show a genetic interaction with GMR-reaper and GMR-grim (data not shown). It appears that the anti-apoptotic activity of the EGFR/Ras1/MAPK specifically counteracts hid-induced apoptosis. The genotypes of flies shown are indicated below each panel.

Figure 6:
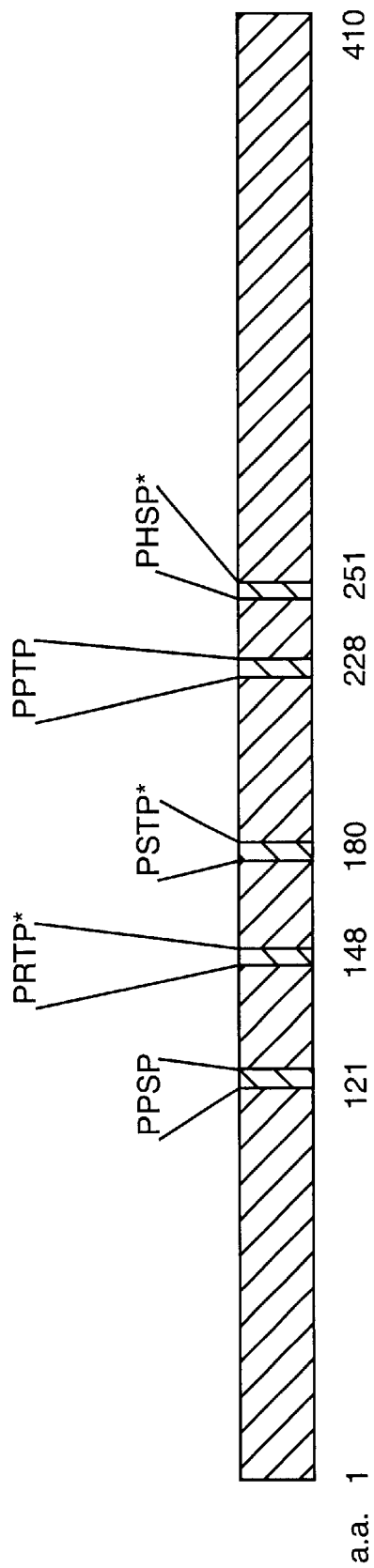

FIG. 6 shows MAPK phosphorylation consensus sites in Hid. The hid gene encodes a novel protein of 410 amino acid residues (Grether et al. "The head involution defective gene of *Drosophila melanogaster* functions in programmed cell death." *Genes Dev.* 9: 1694–1708, 1995). The five MAPK phosphorylation consensus sites are indicated. The consensus site is defined as Pro-X-Ser/Thr-Pro, where X can be any residue except Pro (Clark-Lewis et al., "Definition of a consensus sequence for peptide substrate recognition by p44mpk, the meiosis-activated myelin basic protein kinase", *J. Biol. Chem.* 266: 15180–15184, 1991). In hid$^{Ala5}$, all five phospho-acceptor residues are changed to a non-phosphorylatable residue, Ala. In hid$^{Ala3}$, only Thr$^{148}$, Thr$^{180}$ and Ser$^{251}$ are changed to Ala (indicated by asterisks), since the consensus sites of the remaining two phospho-acceptor residues, Ser$^{121}$ and THr$^{228}$, contain a Pro in the X position.

Figure 7A:
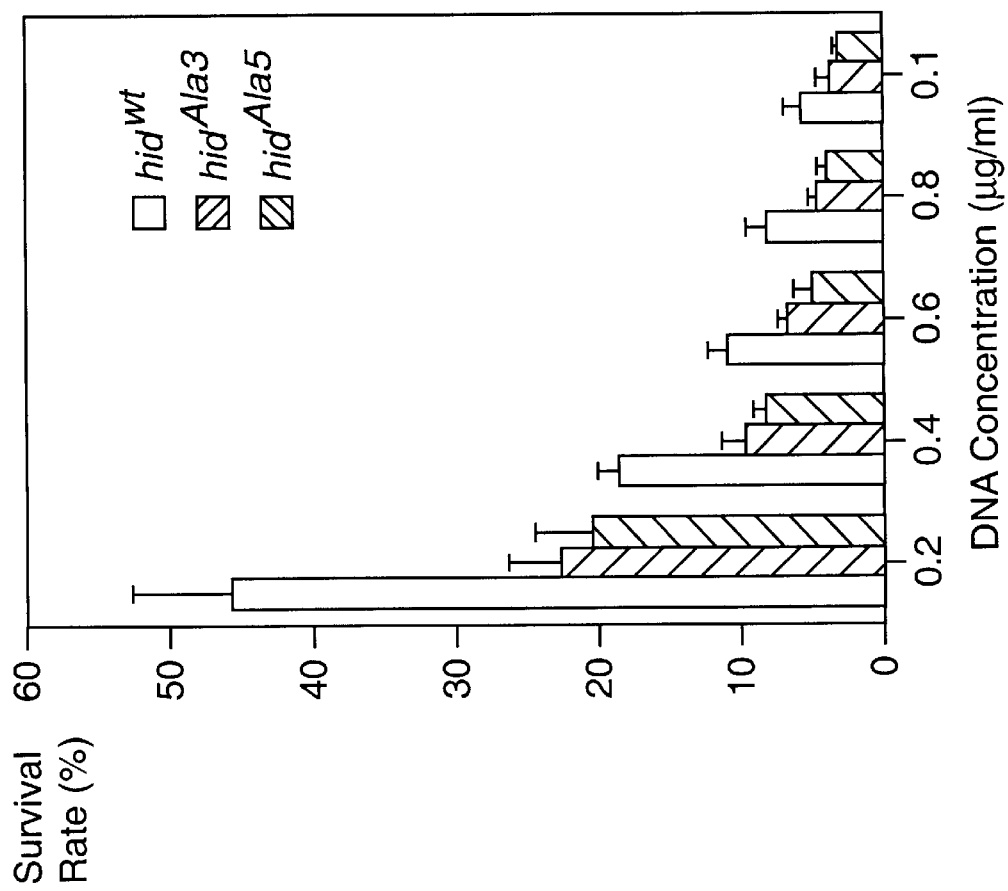
Figure 7C:
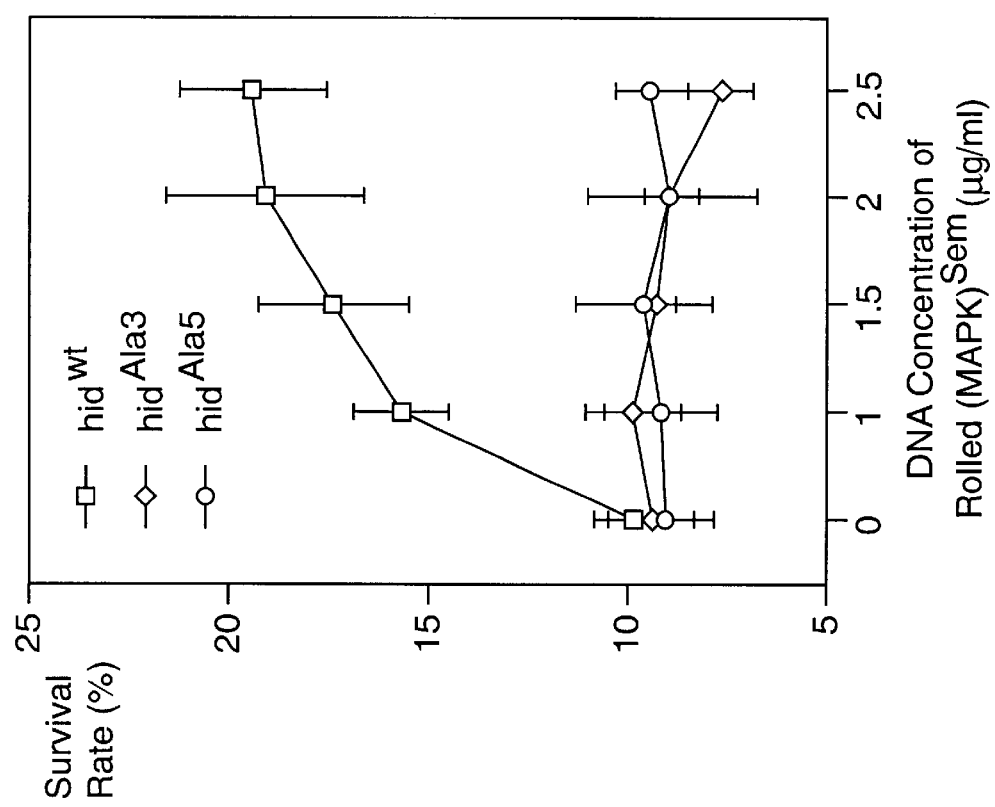
Figure 7B:
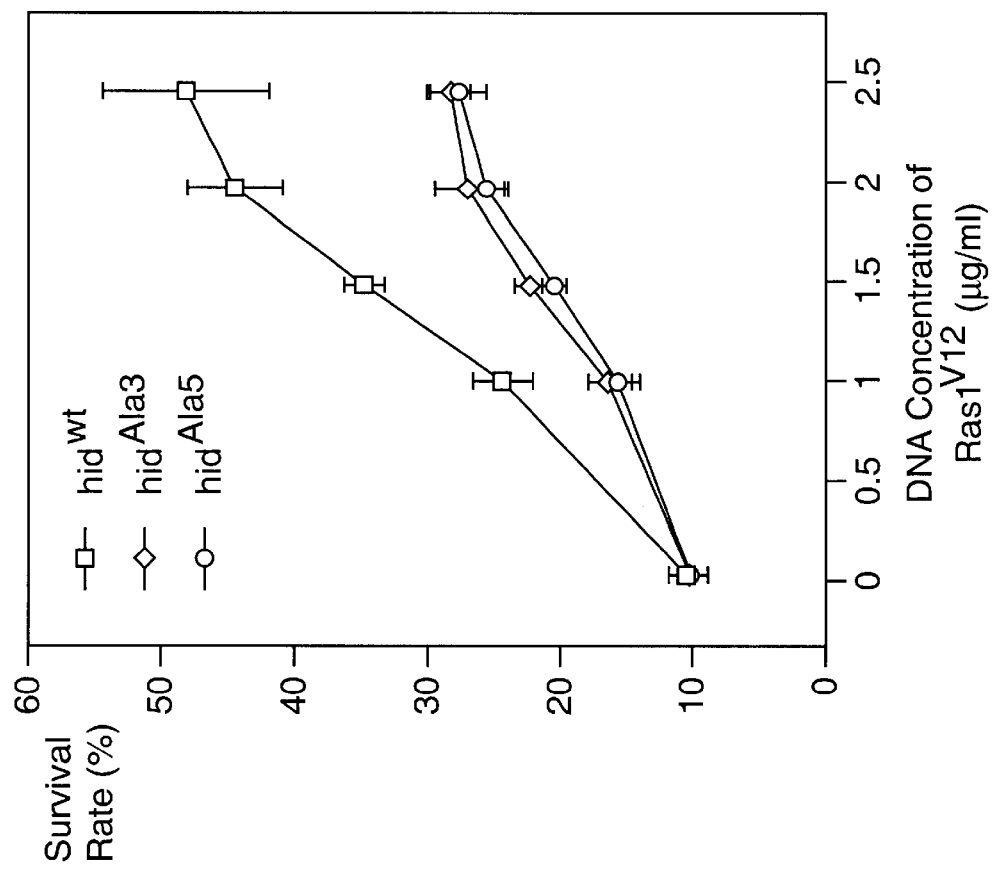

FIG. 7(A–C) shows the effects of MAPK phosphorylation in SL2 cells. SL2 cells were transiently cotransfected with the indicated constructs. (A) The indicated amount of DNA of the Hid constructs was transfected into SL2 cells and tested for their killing activity. The two MAPK site deficient Hid mutants induce apoptotic death more efficiently than does wild-type Hid. (B) Comparison of the rescuing activity of Ras1$^{V12}$ on Hid$^{wt}$-, Hid$^{Ala3}$- and Hid$^{Ala5}$-induced apoptosis in SL2 cells. Constant amounts of DNA of the Hid constructs were cotransfected with increasing amounts of Ras1$^{V12}$ as indicated. Hid$^{wt}$ -induced apoptosis is efficiently blocked by Ras1$^{V12}$, such that the survival rate goes up to about 50%. In contrast the rescuing activity of Ras1$^{V12}$ on Hid$^{Ala3}$- and Hid$^{Ala5}$-induced apoptosis is partially blocked. Only about 28–30% of the cells survive. The amount of the Hid constructs (0.6 μg/ml Hid$^{wt}$; 0.4 μg/ml Hid$^{Ala3}$ and Hid$^{Ala5}$) was determined by FIG. 6A as the amount necessary to allow only 10% of SL2 cells to survive. (C) Similar experiment to FIG. 7B except that increasing amounts of R1$^{Sem}$/MAPK instead of Ras1$^{V12}$ were transfected with constant amounts of the Hid constructs (0.5 μg/ml each). The gof allele R1$^{Sem}$/MAPK behaves also in cultured cells as a suppressor of Hid$^{wt}$-induced apoptosis. Alteration of the MAPK sites in Hid completely abolishes the rescuing activity of R1$^{Sem}$/MAPK on Hid$^{Ala3}$- and Hid$^{Ala5}$-induced apoptosis.

Figure 8:
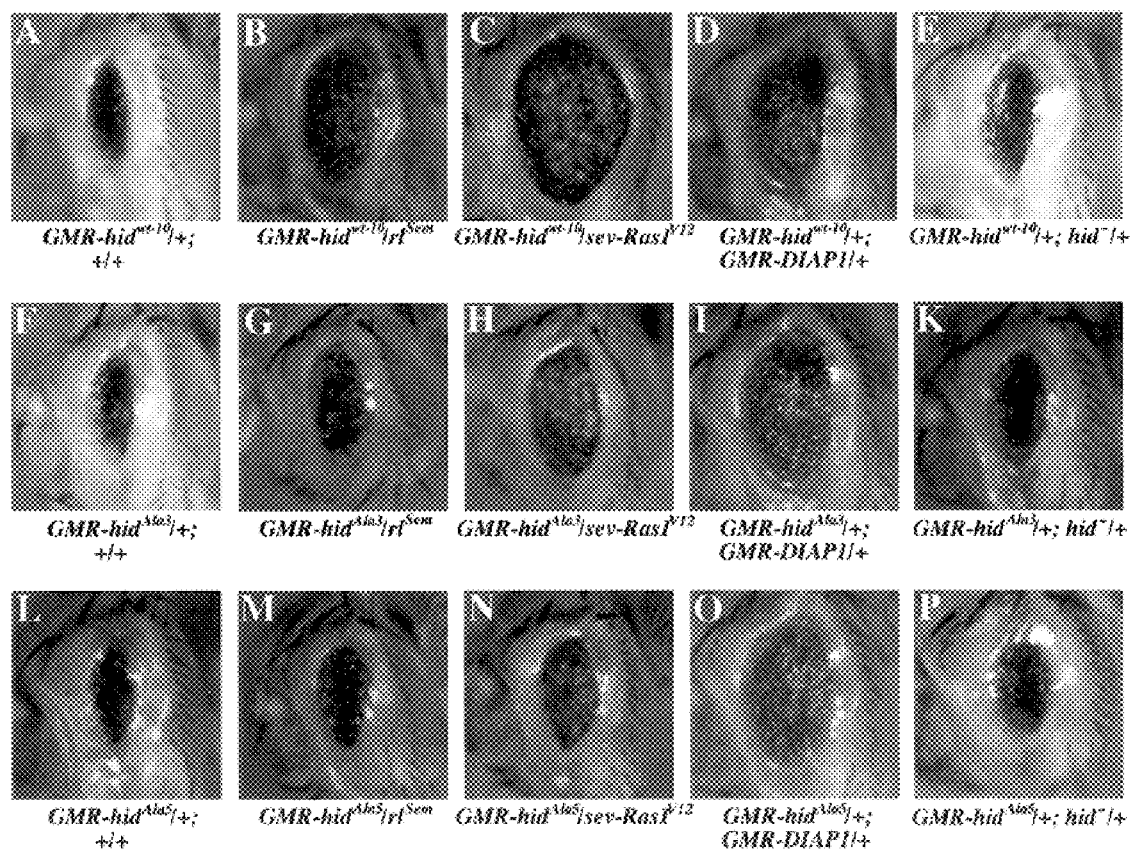

FIG. 8(A–P) shows transgenic analysis of GMR-hid$^{Ala3}$ and GMR-hid$^{Ala5}$. The unmodified eye phenotypes of GMR-hid$^{wt-10}$ (A), GMR-hid$^{Ala3}$ (F) and GMR-hid$^{Ala5}$ (L) are of similar strength allowing direct comparison of the rescuing abilities of rl$^{Sem}$/MAPK (B,G,M), sev-Ras1$^{V12}$ (line CR2; C,H,N), GMR-DIAP1 (D,I,O) and hid$^-$ (E,K,P). Note the block in the ability to suppress the eye ablation phenotype caused by the MAPK deficient GMR-hid transgenes by rl$^{Sem}$/MAPK (G,M) and sev-Ras1$^{V12}$ (H,N), whereas expression of the cell death inhibitor DIAP1 suppresses hid-induced apoptosis independently of the MAPK phosphorylation sites (D,I,O). The weak suppression observed for GMR-hid$^{Ala3}$ and GMR-hid$^{Ala5}$ by rl$^{Sem}$/MAPK (G,M) might be the result of inhibiting endogenous wild-type hid-protein, since removal of one genomic copy of hid results in a weak suppression, too (K,P; see text for explanations). The genotypes of flies shown are indicated below each panel. The hid allele used in E,K,P is hid$^{WR+X1}$.

FIG. 9 shows the DNA sequence of wild type Hid (Hid$^{wt}$, SEQ ID NO:1).

FIG. 10 shows the DNA sequence of Hid$^{Ala3}$ (SEQ ID NO:2).

FIG. 11 shows the DNA sequence of Hid$^{Ala5}$ (SEQ.ID NO:3).

FIG. 12 shows the amino acid sequence of Hid$^{Ala5}$ SEQ ID NO:4. The amino acids changed from the wild type are depicted in FIG. 6.

FIG. 13 shows the amino acid sequence of Hid$^{Ala5}$ SEQ ID NO:5. The amino acids changed from the wild type are depicted in FIG. 6.

DEFINITIONS

To facilitate understanding of the invention, a number of terms are defined below.

The term "gene" refers to a DNA sequence that comprises control and coding sequences necessary for the production of a polypeptide or its precursor. The polypeptide can be encoded by a full length coding sequence or by any portion of the coding sequence.

The term "nucleic acid sequence of interest" refers to any nucleic acid sequence the manipulation of which may be deemed desirable for any reason by one of ordinary skill in the art.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and or functional properties (i.e., altered characteristics) when compared to the wild-type gene or gene product It is noted that naturally-occurring mutants can be isolated; these are identified by the fact that they have altered characteristics when compared to the wild-type gene or gene product.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression construct", "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "hybridization" as used herein refers to any process by which a strand of nucleic acid joins with a complementary strand through base pairing.

As used herein, the terms "complementary" or "complementary" when used in reference to polynucleotides refer to polynucleotides which are related by the base pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions when used in reference to nucleic acid hybridization comprise conditions equivalent to binding or hybridization at 42° C. in a solution consisting of 5X SSPE (43.8 g/l NaCl, 6.9 g/l $NaH_2PO_4 \cdot H_2O$ and 1.85 g/l EDTA, pH adjusted to 7.4 with NaOH), 0.1% SDS, 5X Denhardt's reagent [50X Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5X SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5X SSPE (43.8 g/l NaCl, 6.9 g/l $NaH_2PO_4 \cdot H_2O$ and 1.85 g/l EDTA, pH adjusted to 7.4 with NaOH), 0.5% SDS, 5X Denhardt's reagent and 100 µg/ml denatured salmon sperm DNA followed by washing in a solution comprising 0.1X SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m-5°$ C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "fusion protein" refers to a chimeric protein containing the protein of interest (i.e., Hid and fragments thereof) joined to an exogenous protein fragment (the fusion partner which consists of a non-Hid sequence). The fusion partner may provide a detectable moiety, may provide an affinity tag to allow purification of the recombinant fusion protein from the host cell, or both. If desired, the fusion protein may be removed from the protein of interest by a variety of enzymatic or chemical means known to the art.

As used herein, the term "purified" or "to purify" refers to the removal of contaminants from a sample. The present invention contemplates purified compositions (discussed above).

As used herein the term "portion" when in reference to a protein (as in "a portion of a given protein") refers to fragments of that protein. The fragments may range in size from four amino acid residues to the entire amino acid sequence minus one amino acid.

The term "apoptosis" is understood by those in the art to refer to the morphological changes that are observed in a cell as the cell undergoes a non-accidental death.

The phrase "programmed cell death" as used herein is defined as the term to describe the genetically controlled process that is executed in a cell that has been induced to undergo apoptosis.

The phrase "gain of function" (gof) as used herein is applicable to the situation where a modified oligonucleotide, when transfected into a host organism and translated into a peptide, results in a peptide that will function with increased efficiency (e.g. rate of reaction, affinity, etc.) as compared to the wild type peptide. For example, the modified oligonucleotide (or "lof oligonucleotide") may, in effect, function as an augmenter of the natural gene if the natural gene is present and functional in the host into which the gof oligonucleotide was transfected, or it may add that function to the host if the natural gene is not present or is non-functional.

The phrase "loss of function" (lof) as used herein is applicable to the situation where a modified oligonucleotide, when transfected into a host organism and translated into a peptide, results in a peptide that will function with decreased efficiency (e.g. rate of reaction, affinity, etc.) as compared to the wild type peptide. For example, the modified oligonucleotide (or "lof oligonucleotide") may, in effect, function as a diminisher of natural gene function if the natural gene is present and functional in the host into which the lof oligonucleotide was transfected, or may negatively interfere with processes in the host if the natural gene is not present or is non-functional.

"TUNEL" shall be defined as terminal deoxynucleotidyl transferase (TdT)-mediated FITC-dUTP nick end labeling, a technique to quantitate apoptosis known to those in the field.

"Morphology" shall be defined as the visual appearance of a cell or organism when viewed with the eye, a light microscope or eletronmicroscope, as appropriate.

"Blebbing", in relation to cell morphology, shall be described as a ruffled appearance of the cell surface when the cell is viewed by either light or electron microscopy.

GENERAL DESCRIPTION OF THE INVENTION

The invention generally relates to compositions and methods of identifying and testing agonists and antagonists of Hid phosphorylation, in particular, compositions modifying MAPK phosphorylation of Hid. Additionally, the invention relates to methodologies made possible by the invention to identify new constituents of the cell death process and for the design of drugs, drug therapies and gene therapies that modify the programmed cell death process.

In vivo activation or ectopic expression of Hid result in the apoptotic death of the cell in question. Survival signals initiated at the EGF-receptor or other receptor tyrosine kinase, and propagated through the Ras/MAPK signal pathway, result in the down regulation or elimination of Hid activity, thus preventing apoptotic cell death. Such innate regulatory mechanisms are critical to the proper development and homeostases of an organism. Increased or decreased activation of the MAPK pathway would result in aberrant cell death or survival. Biological processes controlled by apoptosis include remodeling of tissues during embryogenesis, removal of senescent cells, involution of tissues and removal of infected or diseased cells. In cases where regulators of the MAPK pathway have been mutated (e.g. Ras activation in various cancers), cells normally removed via apoptosis would persist.

A. Measurement of Apoptosis—General Indicators

Programmed cell death, or apoptosis, is the genetically controlled, systematic dismantling of a cell. Apoptosis typically happens during embryogenesis when much tissue remodeling is taking place, but continues to happen throughout the life of an organism. For example, the elimination of senescent cells, the involution of tissues and the elimination of diseased cells happens by apoptosis. The hallmarks of the apoptotic process are morphological changes consisting of chromatin condensation, membrane blebbing, loss of membrane integrity and, ultimately, the disintegration of the cell into apoptotic bodies that are engulfed by phagocytic cells. On the molecular scale, DNA is cleaved into 180–200 kb nucleosomal fragments resulting in a laddering appearance when run on an agarose gel. Apoptosis prevents the release of cellular constituents into the extracellular space thereby preventing an inflammatory response and allows for the orderly remodeling of tissues. (In contrast, necrotic or accidental cell death is exemplified by membrane rupture and the release of cellular constituents into the extracellular space resulting in an inflammatory response by the body).

Traditionally, the measurement of apoptosis has been concerned with the accuracy of delineating the percentage of a population undergoing apoptosis, with determining the earliest detectable point in which apoptosis could be accurately detected or with determining the kinetics of the apoptotic process. The changes in morphology and the DNA laddering discussed above, although not overly quantitative, are the classic determinants of apoptosis. Other measures of apoptosis include, but are not limited to, terminal deoxynucleotidyl transferase (TdT)-mediated FITC-dUTP nick end labeling (TUNEL) staining (indicative of early DNA strand cutting by endonucleases), trypan blue stung (and various other vital stains indicative of loss of membrane integrity), propidium iodide (and various other DNA intercalating dyes indicative of loss of DNA from the nucleus) and Annexin-V staining (indicative of phosphatidyl serine exposure on the cell surface). These techniques allow for better quantitative analysis of apoptosis on a population level but only indirectly allow for the measurement of the effect of agonists or antagonists on a specific apoptotic signaling pathway.

B. Measurement of Apoptosis—Cell Pathway Specific Techniques

Some advances have been made into delineating pathway involvement in the apoptotic process. In this regard, inhibitors have been made which target some constituents of the apoptotic pathway. For example, tetra-peptide inhibitors have been developed for several of the caspases activated during apoptosis. Likewise, loss of function and gain of function gene mutants have been made for several steps in the apoptotic process. Additionally, reagents have been developed which combine a fluorogenic substrate with caspase cleavage sites allowing for the visualization of apoptosis-induced caspase activation by flow cytometric methods. These reagents, however, focus on the pro-apoptotic pathways and fail to look at survival pathways.

C. Advances Conferred By The Present Invention

The invention will be used for, among other things, (1) methods to screen for proteins or small molecules that interfere with or augment the phosphorylation of Hid; (2) methods to identify and clone genes that are directly involved in Hid signaling pathways; (3) the identification of new homologs of Hid, for example, from the same or other species; (4) methods for rational drug design; and (5) the development of therapeutic protocols involving the use of (i) Hid interactive compounds to regulate Hid phosphorylation and (ii) the establishment of drug and gene therapies for the treatment of various cancer and autoimmune diseases.

D. Screening Formats i. Cell Based Assays

It is not intended that the present invention be limited to a particular screening format. One embodiment of this invention would be to allow for the transfection of cell lines with plasmids containing the wild type or mutant hid genes and then measure the effect of test compounds on apoptosis. The wild type and mutant hid genes could be inserted in many various plasmids to allow for expression in a wide range of cell types. For example, transfected hid has already been shown to initiate apoptosis in human HeLa cells as well as SL2 insect cells (See Example 4).

ii. Transgenic Animal Based Assays

One embodiment of this invention would be to generate transgenic animals expressing wild type and mutant hid genes to provide an in vivo assay system for the screening of potential drug candidates. The wild type and mutant hid genes could be inserted in many, different available plasmids to allow for expression in a wide range of animals or tissue types (See Example 5).

iii. Immunological Assays

One embodiment of this invention comprises antibodies reactive with (and usually specific for) peptides generated from the wild type and mutant hid genes. This would allow for immunological blotting assays to test for expression in various cell or tissue types, the ability to isolate homologs via immunoprecipitation assays and the ability to purify large quantities of protein from expression systems. Additionally, another embodiment of this invention would be to produce antibodies to phosphorylated vs. non-phosphorylated forms of Hid, based on the mutant forms of Hid that make the basis of this invention, that would provide reagents for an assay method based on Western blotting or intracellular flow cytometric analysis.

iv. Molecular Biological Assays

The present invention contemplates assays utilizing both wild type and mutant hid RNA and DNA. This makes it possible to perform a wild range of standard molecular biological assays including, but not limited to, Northern and Southern blotting, PCR, cloning and various screening assays for the detection of intraspecific and interspecific homologs.

DETAILED DESCRIPTION OF PREFERRED EMBODIMENTS

Generally, the nomenclature used hereafter and the laboratory procedures in cell culture, molecular genetics, and nucleic acid chemistry and hybridization described below are those well known and commonly employed in the art Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references [See, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y.].

Oligonucleotides can be synthesized on an Applied Bio-Systems oligonucleotide synthesizer [for details see Sinha et al., Nucleic Acids Res. 12:4539 (1984)], according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [$g$-$^{32}$P]ATP and T4 polynucleotide kinase Salts and unincorporated nucleotides are removed by chromatography on Sephadex G columns.

The present invention contemplates assays for detecting the ability of agents to inhibit or enhance Hid-mediated apoptosis where high-throughput screening formats are employed together with large agent banks (e.g., compound libraries, peptide libraries, and the like) to identify antagonists or agonists. Such Hid pathway antagonists and agonists may be further developed as potential therapeutics and diagnostic or prognostic tools for diverse types of cancers, autoimmune diseases and hereditary diseases.

1. Screens to identify Agonists of Antagonists of Phosphorylation of Hid

There are several different approaches contemplated by the present invention to look for small molecules that specifically inhibit or enhance the phosphorylation of Hid phosphorylation consensus sites. One approach is to transfect expression constructs comprising nucleic acid encoding Hid mutants into cells and measure changes in the rate of apoptosis as compared to controls after the cells have been exposed to the compound suspected of modulating Hid phosphorylation. Cells may be transiently transfected or stably transfected with the construct under control of an inducible promoter. Other embodiments would include translation of the invention and purification of the peptide. The purified peptide could then be used as a substrate of MAPK phosphorylation in a cell-free kinase assay. $P^{32}$-ATP would be used as a source for phosphate allowing quantitation by autoradiography and phosphorimaging, for example. Additionally, it is possible to generate antibodies to phosphorylated and non-phosphorylated forms of the translated invention allowing for quantitation of phosphorylation of Hid by Western blot. Furthermore, transgenic animal could be produced allowing for in vivo assays to be conducted.

A. In vitro Assays a. Transfection Assays

Transfection assays allow for a great deal of flexibility in assay development. The wide range of commercially available transfection vectors will permit the expression of the Hid mutants of the present invention in a extensive number of cell types. Additionally, Hid has been shown to initiate apoptosis in a number of insect cell types and in mammalian HeLa cells. In one embodiment, cells are transiently transfected with an expression construct comprising nucleic acid encoding Hid mutants of the present invention that included an inducible promotor allowing for the initiation of translation and transcription when needed. Cells would be exposed to the agent suspected of modulating Hid phosphorylation, Hid expression would be turned on and apoptosis would be measured. Rates of apoptosis in cells expressing the invention are compared to rates of apoptosis in cells transfected with a construct expressing a wild type hid gene and cells expressing a control expression vector (e.g. an empty expression vector). Rates of apoptosis can be quantitated by any of a number of ways reported in the literature and known to those practiced in the art.

In another embodiment, stably transfected cells lines are developed, i.e. cell lines stably expressing the Hid mutants of the present invention. The use of an inducible promoter would be utilized in these systems. Screening assays for compounds suspected of modulating Hid phosphorylation would be conducted in the same manner as with the transient transfection assays. Using stably transfected cell lines would allow for greater consistency between experiments and allow for inter-experimental comparisons.

B. In Vivo Assays a. Transgenic Animal Assays

In one embodiment transgenic animals will be constructed using standard protocols (see example 5). The generation of transgenic animals will allow for the investigation of diseases for which the mutated forms of Hid may provide the means for determining the physiology of the disease or its treatment.

2. Screens to Identify Hid Signal Pathway Constituents

A. In vitro Assays

There are several different approaches to identifying Hid interactive molecules. The invention would allow the identification of proteins that only associated with non-phosphorylated Hid molecules. Such proteins may regulate Hid function. Techniques that may be used are, but not limited to, immunoprecipitation of Hid with antibodies generated to the transcription product of the invention. This would also bring down any associated bound proteins. Another method is to generate fusion proteins containing the mutant form of Hid connected to a generally recognized pull-down protein such as glutathione S-transferase. Bound proteins can then be eluded and analyzed.

a. Immunoprecipitation

After the generation of antibodies to wild type and mutant Hids, cells expressing transfected Hid are lysed and then incubated with one of the antibodies. Antibodies with the bound Hid and any associated proteins can then be pulled down with protein-A Sepharose or protein-G Sepharose beads, using standard techniques.

b. Fusion Protein Pulldown

A method similar to immunoprecipitation is to construct fusion proteins of the mutant and wild type Hid and glutathione S-transferase (GS). The GST-Hid fusion proteins are then incubated with cell extracts and then removed with glutathione Sepharose beads. Any bound, Hid-associated proteins are then characterized.

B. In Vio Assays a. Yeast Two-hybrid System

The yeast two-hybrid system that identifies the interaction between two proteins by reconstructing active transcription factor dimers. The dimers are formed between two fusion proteins, one of which contains a DNA-binding domain (DB) fused to the first protein of interest (DB-X) and the other, an activation domain (AD) fused to the second protein of interest (AD-Y). The DB-X:AD-Y interaction reconstitutes a functional transcription factor that activates chromosomally-integrated reporter genes driven by promoters containing the relevant DB binding sites. Large cDNA libraries can be easily screened with the yeast-two hybrid system. Yeast cDNA libraries are commercially available. Standard molecular biological techniques can be employed to isolate and characterize the interacting protein.

3. Screens to Identify Hid Homologs

Standard molecular biological techniques can be used to identify Hid homologs in Drosophila or other species, e.g. mammals. For example, the present invention contemplates a variety of approaches including, but are not limited to, DNA-DNA hybridization techniques (e.g. Southern blots) and DNA-RNA hybridization techniques (e.g. Northern blots). Additional techniques may include, for example, immunoscreening of proteins made from library stocks by antibodies generated from the invention. Additionally, the current invention contemplates taking advantage of the Hid protein interaction with MAPK to isolate and identify Hid homologs. Immunoprecipitation of MAPK may result in the isolation of proteins comprising Hid homologs of the invention. Confirmation of such homologs can be achieved via Southern blotting with corresponding cDNA generated from the invention or Western blotting with antibodies generated to wild type or mutant Hid protein.

EXPERIMENTAL

The following examples serve to illustrate certain preferred embodiments and aspects of the present invention and are not to be constructed as limiting the scope thereof. In the experimental disclosure which follows, the following methodology apply:

Fly stocks

The following mutant and transgenic fly stains were used for phenotypical analysis and genetic interactions: GMR-hid, hs-hid 3, hid$^{WR+X1}$ (Grether et al. "The head involution defective gene of Drosophila melanogaster functions in programmed cells death", Genes Dev. 9:1694–1708, 1995), GMR-hid$^{10}$ sev-GAL4 (this study), GMR-rpr (White et al., "Cell killing by the Drosophila gene reaper", Science 271:805–807, 1996), GMR-grim (Chen et al., "grim, a novel cell death gene in Drosophila", Genes Dev. 10:1773–1782, 1996), GMR-DIAP1 3-1 (Hay et al., "Drosophila homologs of baculovirus inhibitor of apoptosis proteins function to block cell death", Cell 83:1253–1262, 1995), gap1$^{21-1s}$and spry$^{28-4s}$ (this study) arg$^{IA7}$ (Freeman et al, "The argos gene encodes a diffusible factor that regulates cell fate decisions in the Drosophila eye", Cell 69:963–975, 1992), EGFR$^-$= flb$^{f2}$ Nüsslein-Volhard et al., "Mutations affecting the pattern of the larval cuticle in Drosophila melanogaster I. Zygotic loci on the second chromosome", Roux's Arch. Dev. Biol. 193:267–282, 1984), ras$^{DC40b}$ and raf$^{11-29}$ (Hou et al., "The torso receptor tyrosine linase can activate Raf in a Ras-independent pathway", Cell 81:63–71, 1995), rl$^{10a}$ (Peverali et al., "Phosphorylation of Drosophila Jun by MAP kinase rolled regulates photoreceptor differentiation", Embo J. 15:3943–3950, 1996), Elp$^{E1}$ (Baker and Rubin, "Effect on eye development of dominant mutations on Drosophila homologue of the EGF receptor", Nature 340:150–153, 1989), sev-Ras1$^{V12}$ (Fortini et al., "Signalling by the sevenless protein tyrosine kinase is mimicked by Ras1 activation", Nature 355:559–561, 1992), sev-Ras1$^{N17}$ (Karim et al, "A screen for genes that function downstream of Ras1 during Drosophila eye development", Genetics 143:315–329, 1996), sev-Raf$^{torso}$ (Dickson et al., "Raf functions downstream of Ras1 in the Sevenless signal transduction pathway", *Nature* 360:600–603, 1992), rl$^{Sem}$/MAPK (Brunner et al., "A gain-of-function mutation in Drosophila MAP kinase activates multiple receptor tyrosine kinase signaling pathways", *Cell* 76:875–888, 1994), UAS-Ras1$^+$, UAS-Ras1$^{V12S35}$, UAS-Ras1$^{V12G37}$, UAS-Ras1$^{V12C40}$ (Karim and Rubin, "Ectopic expression of activated Ras1 induces hyperplastic growth and increased cell death in Drosophila imaginal tisuues", *Development* 125:1–9, 1998). Flies carrying GMR-hid$^{Ala3}$ and GMR-hid$^{Ala5}$ were generated by P-element mediated transformation. The GMR-hid$^{10}$ sev-GAL4 line was obtained by meiotic recombination. All crosses were performed at 25° C. Flies in all experiments were incubated at 25° C.

hs-hid suppression assay

Offspring of crosses between hs-hid/TM3 and Sup/TM3 (Sup=gap1$^{21-1s}$, spry$^{28-4s}$, arg$^{IA7}$) were heat shocked at 37° C. during first instar larval stage for 10, 20, 30, 40, 50 or 60 min. After recovery, the crosses were incubated at 25° C. After the flies eclosed, the ratio between hs-hid/Sup and Sup/TM3 animals was determined. For rl$^{Sem}$/MAPK, the procedure was similar except that the ratio between rl$^{Sem}$/+;hshid/+ and rl$^{Sem}$/+;+/TM3 was scored. In the control experiment, offspring of a cross between hs-hid/TM3 and +/+ animals were treated as described above, and the ratio between hs-hid/+ and +/TM3 animals was determined. The results presented in FIG. 4 represent the average of three independently performed experiments.

Molecular Biology

In vitro mutagenesis of the MAPK phosphorylation consensus sites in hid was performed using PCR with specifically designed primers. Incorporation of the mutation was confirmed by sequencing. The constructs were subcloned into pGMR1 for P element-mediated transformation and pIE1–3 Novagen, Jarvis et al., "Immediate-early baculovirus vectors for foreign gene expression in transformed or infected insect cells", *Protein Expr. Purif* 8:191–203, 1996) for SL2 cell transfection experiments. The cDNAs encoding Ras1$^{V12}$ and rl$^{Sem}$/MAPK were cloned into pIE1–3 using convenient restriction sites for cell transfections.

SL2 cell transient transfection experiments

SL2 cells (Schneider, "Cell lines derived from late embryonic stage of *Drosophila melanogaster*", *J. Embryol. Exp. Morph* 27:353–365, 1972) were grown in Schneider's Drosophila Medium (Gibco BRL) supplemented with 10% NCS. In each experiment, 100 ng/ml of the reporter plasmid pIE1–3-lacZ (kindly provided by Zhiwei Song) was transfected. Differences in the amount of tester plasmids were compensated for by the addition of empty vector pIE1–3. In three independent experiments transfections were performed using the Cellfectin reagent according to the manufacturer's instructions (Gibco BRL) for 5 h in Serum free medium in 24 well dishes in quadruplicates. 24 h after transfection cells were fixed and stained, and the number of surviving cells was determined.

EXAMPLE 1

Figure 1:
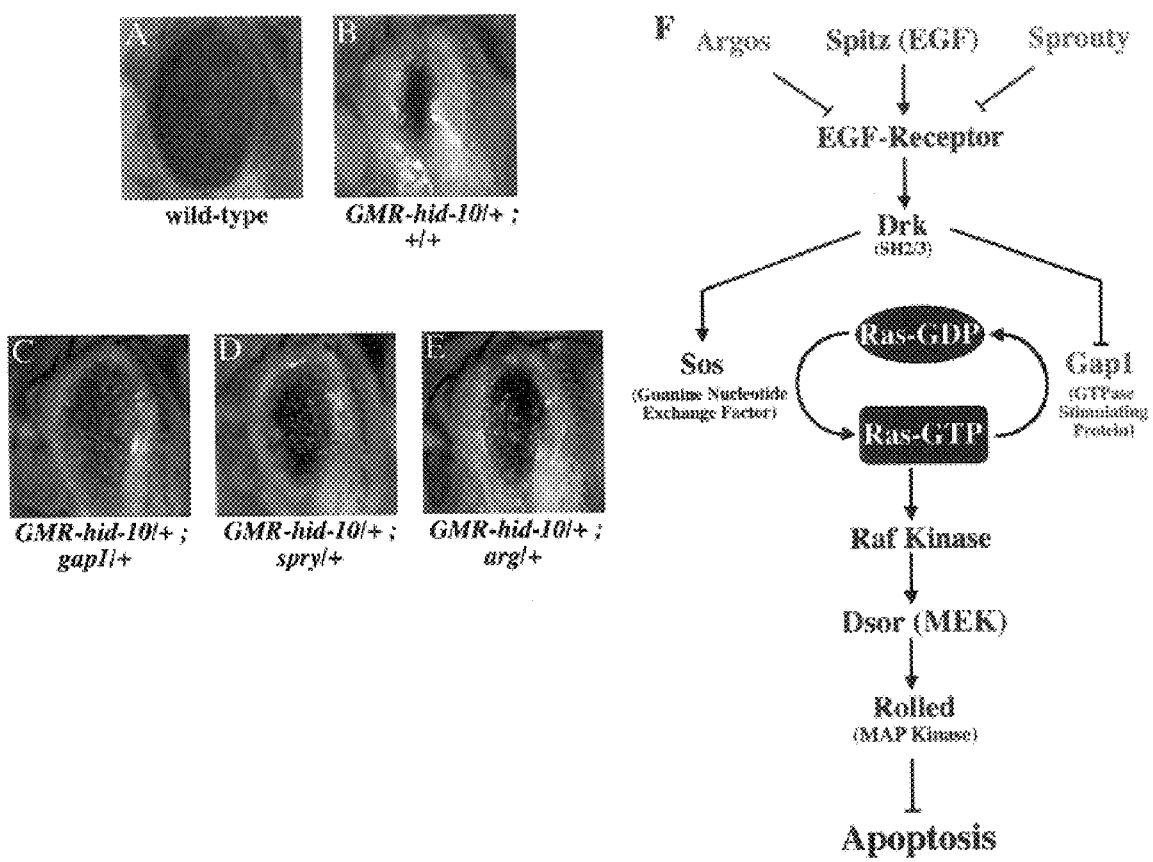
FIG. 1 (A–F) shows that mutations that increase Ras1 signaling suppress Hid induced apoptosis in the compound eye. gap1, spry and arg encode genes that inhibit EGFR/ Ras1 signaling. Mutations in these genes increase Ras1 signaling resulting in suppression of Hid induced apoptosis. Flies in this and all other figures were incubated in parallel at 25° C. throughout development. Compound eyes of females are shown. The genotypes of flies shown are indicated below each panel. All photographs were taken at the same magnification.

In this example data is generated that demonstrates that the ectopic expression of hid, under the control of the eye-specific glass multimer reporter construct (pGMR, Hay et al., "Expression of baculovirus P35 prevents cell death in Drosophila", *Development* 120:2121–2129, 1994; construct designated GMR-hid), drives expression in virtually all cells of the developing eye, beginning at the onset of differentiation in the morphogenetic furrow (Ellis et al., "Expression of Drosophila glass protein and evidence for the negative regulation of its activity in non-neuronal cells by another DNA-binding protein", *Development* 119:855–865, 1993), resulting in eyes which are severely reduced in size and devoid of most normal ommatidial morphology. Compare FIG. 1A (wild-type) with FIG. 1B (GMR-hid$^{10}$/+;+/+) and see Grether et al., 1995. The severity of this eye ablation phenotype is dosage-sensitive; that is flies carrying two copies of the GMR-hid transgene have significantly smaller eyes than flies carrying only one copy (data not shown). The correlation between the degree of hid-activity and the strength of the induced phenotype suggests that a 50% reduction in the dose of a gene involved in hid-mediated apoptosis should result in the visible modification of the eye phenotype caused by GMR-hid. Therefore, using the sensitized GMR-hid background, a genetic F1 screen was performed to isolate mutations in genes which dominantly suppress the GMR-hid-induced eye ablation phenotype. A similar approach has been highly successful for defining a genetic pathway for R7 cell fate determination in the Drosophila eye (Simon et al., "Ras1 and a putative guanine nucleotide exchange factor perform crucial steps in signaling by the sevenless protein tyrosine kinase", *Cell* 67:701–716, 1991; Karim et al., "A screen for genes that function downstream of Ras1 during Drosophila eye development", *Genetics* 143:315–329, 1996; Dickson et al., "Mutations modulating Raf signaling in Drosophila eye development", *Genetics* 142:163–171, 1996). Dominant suppressors were scored by looking for enlarged eye size compared to the unmodified GMR-hid phenotype and are expected to carry mutations in genes which are positively required for Hid-activity. FIGS. 1C–E show dominant suppression of the GMR-hid$^{10}$-induced phenotype by lof mutants in gap1$^{21-1s}$, spry$^{28-4s}$ and arg$^{IA7}$, respectively. In this way, about 300,000 mutagenized F1 progeny were screened and a total of 120 dominant suppressors was isolated.

EXAMPLE 2

In this example data is generated that suggests that mutations in components of the EGFR/Ras/MAPK pathway function as dominant modifiers in the GMR-hid screen. Among known genes, five loss-of-function (lof) alleles of each gap1 and sprouty (spry) were recovered as strong suppressors of GMR-hid in the screen. FIGS. 1C and 1D show dominant suppression of the GMR-hid$^{10}$-induced phenotype by lof mutants in gap1$^{21-1s}$ and spry$^{29-4s}$, respectively. gap1, encoding a GTPase activating protein, was originally identified as a negative regulator of R7 photoreceptor development (Gaul et al, "A putative Ras GTPase activating protein acts as a negative regulator of signaling by the Sevenless receptor tyrosine kinase", *Cell* 68:1007–1019, 1992) and appears to function by stimulating the GTPase-activity of Ras1 causing Ras1 to hydrolyze GTP to GDP and thereby returning it to its inactive conformation. Sprouty was originally identified as an inhibitor of tracheal branding by antagonizing the Drosophila FGF RTk pathway and encodes a novel, presumably secreted polypeptide (Hacohen et al., "sprouty encodes a novel antagonist of FGF signaling that patterns apical branching of the Drosophila airways", *Cell* 92:253–263, 1998). Both genes are believed to negatively regulate RTK/Ras1 signaling. Gap1 promotes the GTPase-activity of Ras1. Another gene, argos (arg$^{IA7}$), known to negatively regulate EGF-Receptor (EGFR) signaling (Freeman et al., "The argos gene encodes a diffusible factor that regulates cell fate decisions in the Drosophila eye, *Cell* 69:963–975, 1992; Okano et al., "Regulation of Drosophila neural development by a putative secreted protein", *Differentiation* 52:1–11, 1992), was also found to suppress the GMR-hid-induced eye ablation phenotype (FIG. 1E).

FIG. 1F shows a schematic drawing of the EGFR/Ras/MAPK signaling pathway and the relative position of the inhibitory genes gap1, argos and sprouty. Arg and Spry are secreted polypeptides which inhibit EGFR activation. Gap1 promotes the GTPase-activity of Ras1. Abbreviations used in FIG. 1F:EGF (epidermal growth factor), Drk (downstream of receptor kinase), Sos (Son of sevenless), Dsor (downstream suppressor of rat), MAPK (mitogen activated protein kinase), MEK (MAPK-Erk kinase).

The wild-type function of the genes gap1, spry and arg is required to inhibit EGFR/Ras1 signaling. Mutations in any one of these genes increase the signaling strength of the EGFR/Ras1 pathway. Thus, recovery of mutants in these genes as potent suppressors of the GMR-hid-induced eye phenotype indicates that the EGFR/Ras1 signaling pathway has an anti-apoptotic effect by inhibiting hid-activity. To test this notion, we studied the consequence of both loss-of-function (lof) and gain-of-function (gof) mutants of components of the Ras1 pathway on GMR-hid. The results for these experiments are in FIG. 2. The genotypes of the flies are indicated below each panel. Two different GMR-hid transgenic lines were used in this analysis. GMR-hid line 1M (GMR-hid$^{1M}$) causes a mild eye ablation phenotype (FIG. 2A) and was used to score for enhancement by Ras1 pathway mutants. GMR-hid line 10 (GMR-hid$^{10}$) causes a strong eye ablation phenotype (FIG. 2G) and was used to score for suppression by Ras1 pathway mutants.

The results obtained are consistent with our previous findings. Reduction of Ras1 pathway activity leads to enhancement of GMR-hid-induced killing activity. Lof alleles of the EGF-Receptor, ras1, raf and rolled (rl), the Drosophila MAPK homolog (referred to as rl/MAPK), enhance GMR-hid$^{1M}$-induced apoptosis (FIG. 2). The strongest enhancement of GMR-hid$^{1M}$, however, was caused by a dominant negative allele of ras1, ras1$^{N17}$, placed under eye-specific sevenless promoter control (sev-Ras1$^{N17}$; Karim et al., "A screen for genes that function downstream of Ras1 during Drosophila eye development", Genetics 143:315–329, 1996; FIG. 2D).

The opposite effect was observed when gof alleles of EGFR, ras1, raf and rl/MAPK were tested against GMR-hid$^{10}$. The gof alleles of both Ras1 and Raf are transgenes which were placed under control of the eye-specific promoter of the sevenless gene (sev-Ras1$^{V12}$, sev-Raf$^{torso}$). Their gof character was determined by the ability to induce supernumerary R7 cells in the absence of RTK signaling (Fortini et al., "Signalling by the sevenless protein tyrosine kinase is mimicked by Ras1 activation", Nature 355:559–561, 1992; Dickson et al., "Raf functions downstream of Ras1 in the Sevenless signal transduction pathway", Nature 360:600–603, 1992). The sev-Ras1$^{V12}$ transgenes contain a valine for glycine substitution at residue 12 which renders Ras1 constitutively active and bypasses the requirement for RTK activation (Fortini et al., "Signalling by the sevenless protein tyrosine kinase is mimicked by Ras1 activation", Nature 355:559–561, 1992). Two independent sev-Ras1$^{V12}$ transformants, designated CR2 and T2B (Karim et al., "A screen for genes that function downstream of Ras1 during Drosophila eye development", Genetics 143:315–329, 1996), showed very strong suppression of the GMR-hid$^{10}$-induced eye phenotype (FIG. 2I,K). Activating Raf in sev-Raf$^{torso}$ is achieved by targeting Raf to the membrane by fusing the kinase domain of Raf to the transmembrane and extracellular domain of the RTK torso (Dickson et al., "Raf functions downstream of Ras1 in the Sevenless signal transduction pathway", Nature 360:600–603, 1992). The sev-Raf$^{torso}$ transgene tested in this study shows a strong suppression of GMR-hid$^{10}$ (FIG. 2L).

Whereas the gof alleles of Ras1 and Raf are transgenes, the gof alleles of the EGFR (Elp$^{E1}$) and of rl/MAPK (rl$^{Sem}$, Sem-Sevenmaker) are mutations in the endogenous genes (Baker and Rubin, "Effect on eye development of dominant mutations in Drosophila homologue of the EGF receptor", Nature 340:150–153, 1989; Brunner et al., "A gain-of-function mutation on Drosophila MAP kinase activates multiple receptor tyrosine kinase signaling pathways", Cell 76:875–888, 1994). For instance, the RTK independent activation by the Sevenmaker allele of rl/MAPK is caused by a single amino acid substitution (Asp to Asn at position 334, Brunner et al., "A gain-of-function mutation on Drosophila MAP kinase activates multiple receptor tyrosine kinase signaling pathways", Cell 76:875–888, 1994). Thus, it appears that the strong suppression of GMR-hid$^{10}$ by rl$^{Sem}$/MAPK (FIG. 2M) is not caused by a simple overexpression effect but rather by specific activation of the rl$^{Sem}$/MAPK gene product. We also saw strong suppression of GMR-hid$^{10}$-induced apoptosis by expression of secreted spitz, the activated form of the EGF ligand encoded by the spitz gene (data not shown; Schweitzer et al., "Secreted Spitz trggers the DER signaling pathway and is a limiting component in embryonic ventral ectoderm determination", Genes Dev 9:1518–1529, 1995).

In the GMR-hid suppression assay, we detected a slightly stronger suppression of hid-induced apoptosis by the sev-Ras1$^{V12}$ transgenes compared to the suppression obtained by rl$^{Sem}$/MAPK (compare FIG. 2I and K with FIG. 2M). This suggests that in addition to MAPK signaling, other Ras1-dependent survival mechanisms may operate to inactivate hid-activity. Active, GTP-bound Ras transduces signals through multiple intracellular targets including (among others) Raf (at the apex of the MAPK pathway), the p110 catalytic subunit of PI3-Kinase (activating the Akt-1 kinase) and Ral.GDS, the exchange factor for Ra1.GTPases. FIG. 3A shows a schematic outline of the downstream effector pathways of Ras1 and of the effector loop mutations in Ras1 leading specifically to activation of only one effector branch. We investigated the relative contributions made by each of these effectors on suppression of hid-induced apoptosis. We used partial lof mutants located in the Ras effector loop that each activate only one of the downstream pathways mentioned above. Each mutant resides in a constitutively activated Ras1$^{V12}$ background, such that the mutant Ras1$^{V12S35}$ interacts with Raf, but fails to interact with PI3-K or Ral.GDS; Ras1$^{V12G37}$ interacts with Ra1.GDS, but not with Raf or PI3-K; the Ras1$^{V12C40}$ mutant interacts with PI3-K, but not with Raf or Ral.GDS (FIG. 3A; Rodriguez-Viciana et al., "Role of phosphoinositide 3-OH kinase in cell transformation and control of the actin cytoskeleton by Ras", Cell 89457–467, 1997; Karim and Rubin, "Ectopic expression of activated Ras1 induces hyperplastic growth and increased cell death in Drophophila imaginal tissues", Development 125:1–9, 1998; White et al., "Multiple Ras functions can contribute to mammalian cell transformation", Cell 80:533–541, 1995). We used the GAL4-UAS system (Brand and Perrimon, "Targeted gene expression as a means of altering cell fates and generating dominant phenotypes", Development 118:401–415, 1993) to express wild-type Ras1 and the Ras1 mutants under sev promoter control (sev-GAL4) specifically in eye imaginal discs. The genotypes for FIGS. 3B–F are as follows: (B) GMR-hid$^{10}$ sev-GAL4/+; (C) GMR-hid$^{10}$ sev-GAL4/UAS-Ras1$^+$; (D) GMR-hid$^{10}$ sev-GAL4/UAS-Ras1$^{V12S35}$; (E) GMR-hid$^{10}$ sev-GAL4/UAS-Ras1$^{V12G37}$; (F) GMR-hid$^{10}$ sev-GAL4/UAS-Ras1$^{V12C40}$. FIG. 3B shows the eye ablation phenotype caused by GMR-hid$^{10}$ sev-Gal4. FIG. 3C shows that wild-type Ras1 does not modify the GMR-hid[10] eye phenotype. This analysis showed that the Raf/MAPK branch provides the major suppression of hid-induced apoptosis (FIG. 3D). The Ral.GDS effector pathway failed to contribute to the survival activity of Ras1 (FIG. 3E). A moderate suppression of hid-induced apoptosis was provided by the PI3-K/Akt-kinase branch (FIG. 3F), consistent with its previously reported anti-apoptotic function (Kennedy et al., "The PI 3-kinase/Akt signaling pathway delivers an anti-apoptotic signal", *Genes Dev.* 11:701–713, 1997; Yao and Cooper, "Requirement for phosphatidylinositol-3 kinase in the prevention of apoptosis by nerve growth factor", *Science* 267:2003–2006, 1995; Staveley et al., Genetic analysis of protein kinase B (AKT) in. Drosophila", *Curr. Biol.* 8:599–602, 1998). Thus, it appears that Ras1 mediates its survival activity largely through the MAPK pathway, supplemented by a minor component of the PI3-K/Akt-kinase branch.

To further characterize the survival activity of the EGFR/Ras1/MAPK pathway on Hid-induced cell death, we sought for an alternative assay in a different developmental context. Induction of hid under control of a heat shock promoter (hs-hid) very efficiently causes organismal lethality (Grether et al., "The head involution defective gene of *Drosophila melanogaster* functions in programmed cell death", *Genes Dev.* 9:1694–1708, 1995). Only about 2% of the animals containing a hs-hid transgene survive to adulthood compared to control (non hs-hid) flies after they received a 30 min heat shock at 37° C. during the first instar larval stage (FIG. 4). A 40 min heat shock under the same conditions was sufficient to kill all hs-hid containing animals.

However, in a heterozygous mutant background for the genes gap1, spry and arg the hs-hid-induced lethality is strongly reduced such that approximately 20–40% of hs-hid transgenic animals survive even after a 60 min heat shock at 37° C. during first instar larval stage (FIG. 4). An even more striking rescue is observed if the hs-hid suppression assay is performed with the gof rl$^{Sem}$/MAPK allele (see above; Brunner et. al., "A gain-of-function mutation in Drosophila MAP kinase activates receptor tyrosine kinase signaling pathways", *Cell* 76:875–888, 1994). After 60 min of heat shock 70–80% of hs-hid transgenic flies survive (FIG. 4). The genotype of flies analyzed in this assay are +/hs-hid (open square), gap1$^{21-1s}$/hs-hid (open diamond), spry$^{28-4s}$/hs-hid (open circle), arg$^{IΔ7}$/hs-hid (open triangle) and rl$^{Sem}$/+; hs-hid/+(closed square). The results shown represent the average of three independently performed experiments.

In summary, the observed genetic interaction strongly suggests that activation of the EGFR/Ras1/MAPK pathway inactivates the death inducing ability of the pro-apoptotic gene hid.

EXAMPLE 3

In this example the data suggests that the EGFR/Ras/MAPK pathway acts specifically on Hid and does not influence Reaper- and Grim-induced killing. We also studied the influence of the EGFR/Ras1/MAPK pathway on the other two known death effector genes in Drosophila, reaper and grim. In FIG. 5, we compare the enhancing and suppressing effects of the dominant negative sev-Ras1$^{N17}$ allele and the gof sev-Ras1$^{V12}$ allele, respectively, on GMR-reaper- and GMR-grim-induced eye phenotypes. These two Ras1 alleles gave the strongest effects on GMR-hid-induced apoptosis (FIG. 2D,I,K). However, the eye ablation phenotypes of both GMR-reaper and GMR-grim are not significantly affected by the Ras1 mutants. This finding is further confirmed by analysis of other pathway mutants (data not shown). FIG. 5 shows the mild eye ablation phenotypes caused by one copy of GMR-reaper (A) and GMR-grim (C) that were used to score for an enhancement by the dominant-negative Ras1 allele sev-Ras1$^{N17}$ (B and D). Stronger eye ablation phenotypes were produced by two copies of either GMR-reaper (E) or GMR-grim (G), and were used to test for suppression by the gof Ras1 allele sev-Ras1$^{V12}$ (F and H). Both Ras1 transgenes, sev-Ras1$^{N17}$ and sev-Ras1$^{V12}$, do not or only weakly modify either the GMR-rpr- or GMR-grim-induced eye phenotypes. These Ras1 transgenes show striking effects on GMR-hid-induced apoptosis (see FIG. 2D and 2I). Other EGFR/Ras1/MAPK pathway mutants also fail to show a genetic interaction with GMR-reaper and GMR-grim (data not shown). We conclude that the anti-apoptotic activity of the EGFR/Ras1/MAPK specifically counteracts hid-induced apoptosis. The genotypes of flies shown are indicated below each panel. Thus, in summary, the anti-apoptotic survival activity of the Ras1 pathway is predominantly mediated by specific inactivation of the death effector gene hid. In the following, we address the molecular mechanisms of this effect.

EXAMPLE 4

In this example the data suggest that alteration of MAPK sites of Hid blocks the survival abilities of Ras1$^{v12}$ and R1$^{Sem}$/MAPK in SL2 cells. Since in both the GMR-hid and the hs-hid suppression assays, hid is placed under heterologous promoter control, we assumed that the EGFR/Ras1/MAPK pathway suppresses hid-activity at a post-translational level. The presence of five MAPK phosphorylation consensus sites in the hid protein suggested the possibility that Hid is a direct target of MAPK phosphorylation (FIG. 6). Three known phosphorylation targets of MAPK in Drosophila are Yan, which contains eight phosphorylation consensus sites (Rebay and Rubin, "Yan functions as a general inhibitor of differentiation and is negatively regulated by activation of the Ras1/MAPK pathway", *Cell* 81:857–866, 1995), D-Jun (three consensus sites, Peverali et al., "Phosphorylation of Drosophila Jun by the MAP kinase rolled regulates photoreceptor differentiation", *Embo J* 15:3943–3950, 1996) and Pointed P2, (one such sequence, Brunner et al., "The ETS domain protein pointed-P2 is a target of MAP kinase in the sevenless signal transduction pathway", *Nature* 370:386–389, 1994). Whereas D-Jun and Pointed P2 are activated via phosphorylation by MAPK, the Yan protein is inactivated in response to MAPK signaling (Peverali et al., "Phosphorylation of Drosophila Jun by the MAP kinase rolled regulates photoreceptor differentiation", *Embo. J.* 15:3943–3950, 1996; Brunner et al., "The ETS domain protein pointed-P2 is a target of MAP kinase in the sevenless signal transduction pathway", *Nature* 370:386–389, 1994; ). By analogy to Yon, we considered that phosphorylation of Hid protein by MAPK leads to its inactivation and is the cause for the observed genetic effects.

To investigate this hypothesis, we used in vitro mutagenesis to replace the phospho-acceptor residues of the consensus sites with a non-phosphorylatable amino acid, alanine. If downregulation of hid-activity occurs via phosphorylation by MAPK, then removal of the phosphorylation sites should result in a mutant form of Hid that fails to respond to Ras1/MAPK signaling. We constructed two different MAPK deficient mutants of hid. The consensus site is defined as Pro-X-Ser/Thr-Pro, where X can be any residue except Pro (Clark-Lewis et al., "Definition of a consensus sequence for peptide substrate recognition by p44mpk, the meiosis-activated myelin basic protein kinase", *J. Biol. Chem.* 266:15180–15184, 1991). In hid$^{Ala5}$ all five Ser/Thr were changed to Ala. In hid$^{Ala3}$ only Thr$^{148}$, Thr$^{180}$ and Ser$^{251}$ were changed to Ala (indicated with asterisks in FIG. 6) since the consensus sites of the remaining two phosphoacceptor residues, Ser$^{121}$ and Thr$^{228}$, contain a Pro in the X position.

First, we tested the biological activity of these mutant constructs in a rapid cell culture assay. Schneider line 2 cells (SL2), a Drosophila cell line (Schneider, "Cell lines derived from late embryonic stages of *Drosophila melanogaster*", J. Embryol. Exp. Morph 27:353–365, 1972), were transiently transfected with hid$^{wt}$, hid$^{Ala3}$ and hid$^{Ala5}$. The genes were expressed under control of the constitutively active ie1 promoter from baculovirus (Jarvis et al., "Immediate-early baculovirus vectors for foreign gene expression in transformed or infected cells", *Protein Expr. Purif.* 8:191–203, 1996). Transfection of the mutant constructs resulted in much stronger killing activity than transfection of the wild-type construct (FIG. 7A: hid$^{wt}$, grey speckled bar; hid$^{Al3}$, stripped bar; hid$^{Ala5}$, hatched bar). Therefore, the two hid mutants behave as gof alleles of hid. To explain the gof characteristics of the hid mutants in SL2 cells we assume that they are not responsive to Ras1/MAPK signaling due to the change of the MAPK phosphorylation sites of Hid. The components of the Ras1 pathway are present in SL2 cells as shown by transcriptional assays of other target genes of the pathway like pointed and yan (O'Neill et al., "The activities of two Ets-related transcription factors required for Drosophila eye development are modulated by the Ras/MAPK pathway", *Cell* 78:137–147, 1994; Rebay and Rubin, "Yan functions as a general inhibitor of differentiation and is negatively regulated by activation of the Ras1/MAPK pathway", *Cell* 81:857–866, 1995). Survival factors provided by the medium may trigger activation of the Ras1 pathway leading to inactivation of Hid$^{wt}$. The Hid mutants, however, are not responsive to MAPK signaling anymore and thus behave as more efficient inducers of cell death in these cells.

To test the survival requirement of Ras1/MAPK on Hid-induced cell death we transiently co-transfected the hid constructs with cDNAs encoding Ras1$^{V12}$ and R1$^{Sem}$/MAPK under ie1 promoter control into Schneider SL2 cells. Consistent with the genetic findings both Ras1$^{V12}$ and R1$^{Sem}$/MAPK suppress cell death induced by Hid$^{wt}$ in SL2 cells (FIG. 7B and C: hid$^{wt}$, open square; hid$^{Ala3}$, open diamond; hid$^{Ala5}$, open circle). FIG. 7B compares the rescuing activity of Ras1$^{V12}$ on Hid$^{wt}$-, Hid$^{Ala3}$- and Hid$^{Ala5}$-induced apoptosis in SL2 cells. Constant amounts of DNA of the Hid constructs were cotransfected with increasing amounts of Ras1$^{V12}$ as indicated. Hid$^{wt}$-induced apoptosis is efficiently blocked by Ras1$^{V12}$, such that the survival rate goes up to about 50%. In contrast, the rescuing activity of Ras1$^{V12}$ on Hid$^{Ala3}$- and Hid$^{Ala5}$- induced apoptosis is partially blocked. Only about 28–30% of the cells survive. The amount of the Hid constructs (0.6 μg/ml Hid$^{wt}$; 0.4 μg/ml Hid$^{Ala3}$ and Hid$^{Ala5}$) was determined by FIG. 6A as the amount necessary to allow only 10% of SL2 cells to survive. FIG. 7C shows a similar experiment to FIG. 7B except that increasing amounts of R1$^{Sem}$/MAPK instead of Ras1$^{V12}$ were transfected with constant amounts of the Hid constructs (0.5 μg/ml each). The survival rescue provided by Ras1$^{V12}$ is quantitatively much stronger than that provided by R1$^{Sem}$/MAPK. Increasing concentrations of Ras1$^{V12}$ in this assay resulted in an up to 5 fold increase in the number of surviving SL2 cells, whereas R1$^{Sem}$/MAPK reduces the killing activity of Hid$^{wt}$ only about 2 fold (FIG. 7B and C). This difference in the survival abilities of Ras1 and R1/MAPK has previously been observed in the GMR-hid suppression assay (FIG. 2) and might reflect activation of the PI3-K/Akt effector branch of Ras1 as seen in FIG. 3.

In the cotransfection experiment performed with the mutants Hid$^{Ala3}$ and Hid$^{Ala5}$, the survival ability of Ras1$^{V12}$ on the mutants is significantly weaker as compared to Hid$^{wt}$. The number of surviving SL2 cells is increased only 2.5 fold in the Hid$^{Ala3/5}$ experiment compared to a 5 fold increase in the Hid$^{wt}$ experiment (FIG. 7B). The weak rescue seen in this experiment might be the result of activation of the PI3-K/Akt-kinase effector branch (see FIG. 3). However, alteration of the MAPK sites of Hid completely abrogates the survival ability of R1$^{Sem}$/MAPK on Hid-induced cell death in this assay (FIG. 7C). The mutants Hid$^{Ala3}$ and Hid$^{Ala5}$ appear insensitive to MAPK signaling. These results indicate that changing the Ser/Thr residues in the MAPK sites of Hid is sufficient to render the hid protein insensitive to R1/MAPK signaling under these assay conditions and is consistent with our assumption that the MAPK sites are critical for the observed survival activity of Ras1/MAPK signaling on hid-induced apoptosis.

EXAMPLE 5

In this example, establishment of GMR-hid$^{Ala3}$ and GMR-hid$^{Ala5}$ allowed the generation of data that was consistent with the finding in example 3 and strongly supports a model according to which the activity of the cell death regulator hid is modulated by MAPK signaling in vivo. In order to study the hid$^{Ala3}$ and hid$^{Ala5}$ mutants in vivo we generated GMR based constructs, designated GMR-hid$^{Ala3}$ and GMR-hid$^{Ala5}$, and established transgenic lines using P element mediated transformation.

In total, six GMR-hid$^{Ala3}$ and four GMR-hid$^{Ala5}$ transgenic lines were obtained. While the strength of the eye ablation phenotype caused by GMR-hid$^{wt}$ ranges from mild to severe defects (compare GMR-hid$^{wt-1M}$ with GMR-hid$^{wt-10}$ in FIG. 2), all of the GMR-hid$^{Ala3}$ and GMR-hid$^{Ala5}$ lines produce a severe eye ablation phenotype (FIG. 8; the genotype of flies shown are indicated below each panel. The hid allele used in E,K,P is hid$^{WR+XI}$), with some lines completely lacking eye structures (data not shown). These strong phenotypes are presumably caused by a failure of Ras1/MAPK signaling to suppress the MAPK deficient GMR-hid mutants, since Ras1 signaling plays an essential role during eye development (reviewed in Freeman, "Cell determination strategies in the Drosophila eye", Development 124:261–270, 1997).

To further confirm this notion, we analyzed the effect of the gain-of-function rl$^{Sem}$/MAPK allele on GMR-hid$^{Ala3}$ and GMR-hid$^{Ala5}$. Based on the results obtained in SL2 cells (see FIG. 7) we did not expect to detect a suppression of the GMR-hid$^{Ala3}$- and GMR-hid$^{Ala5}$-induced eye phenotype by activated forms of MAPK. Several lines were tested and gave identical results. Flies expressing GMR-hid$^{Ala3}$ and GMR-hid$^{Ala5}$ in a rl$^{Sem}$/MAPK mutant background show a mildly suppressed eye phenotype (FIG. 8G,M). The extent of this suppression is much weaker compared to the one obtained for GMR-hid$^{wt-10}$ (FIG. 8B). Also, the sev-Ras1$^{V12}$ transgenes largely fail to suppress the eye ablation phenotype caused by the MAPK site deficient GMR-hid transformants (FIG. 8H, N). This result indicates that MAPK signaling inactivates the cell death inducing activity of hid. However, the GMR-hid$^{Ala3}$and GMR-hid$^{Ala5}$-induced eye phenotypes are still partially suppressed by activated forms of MAPK. This partial suppression might be caused by inactivation of the endogenous hid wild-type protein that is provided by the two genomic copies, which are widely expressed in the developing eye (Grether, "Molecular Genetic Analysis of Larval Visual System Development and Programmed Cell Death in Drosophila", Thesis, Massachusetts Institute of Technology, Cambridge, Mass., 1994). Reduction of the endogenous hid gene dose by 50% (i.e. a heterozygous hid mutant background) resulted in weak suppression of the GMR-hid$^{wt}$, GMR-hid$^{Ala3}$ and GMR-hid$^{Ala5}$ eye phenotypes (FIG. 8E, K, P). Thus, the endogenous hid gene adds to the full GMR-hid-induced eye phenotype. Since its gene product is expected to be fully responsive to Ras1/MAPK signaling, it is likely that the weak suppression of GMR-hid$^{Ala3}$ and GMR-hid$^{Ala5}$ by activated forms of MAPK is caused by inactivation of the endogenous hid gene.

In control crosses, we tested transgenes of and mutations in specific cell death genes which are not involved in Ras1/MAPK signaling. The well characterized gene diap1 (Drosophila inhibitor of apoptosis protein) under GMR promoter control (GMR-DIAP1, Hay et al., "Drosophila homologs of baculovirus inhibitor of apoptosis proteins function to block cell death", Cell 83:1253–1262, 1995), suppressed the eye ablation phenotypes caused by GMR-hid$^{wt}$, GMR-hid$^{Ala3}$ and GMR-hid$^{Ala5}$ to a similar extent (FIG. 8D, I, O). Other control crosses included GMR-p35, a general inhibitor of apoptosis (Hay et al., "Expression of P35 prevents cell death on Drosophila", Development 120:2121–2129, 1994, Clem et al., "Prevention of apoptosis by a baculovirus gene during infection of insect cells", Science 254:1388–1390, 1991), dominant suppressors recovered in the GMR-hid suppressor screen, and mutations in glass, which encodes a transcription factor which activates transcription from the GMR promoter and is expected to influence GMR transgenes similarly. As with GMR-DIAP1, in these crosses, the eye ablation phenotypes caused by GMR-hid$^{wt}$, GMR-hid$^{Ala3}$ and GMR-hid$^{Ala5}$ are suppressed to a similar extent (data not shown). The findings in these control crosses further support the notion that the failure to suppress GMR-hid$^{Ala3}$ and GMR-hid$^{Ala5}$ by active MAPK is due to the lack of MAPK phosphoacceptor sites in Hid.

In summary, our mutational analysis provides strong evidence that the MAPK phosphorylation consensus sites of Hid are critical for the observed survival activity of the Ras1/MAPK pathway on Hid-induced apoptosis. Thus, it appears that active MAPK suppresses Hid by direct phosphorylation.

We claim:

1. An isolated and purified polynucleotide sequence selected from the group consisting of:
   a) a Hid$^{Ala3}$ cDNA molecule that comprises the nucleotide sequence set forth in Seq. Id. No. 2; and
   b) a Hid$^{Ala5}$ cDNA molecule that comprises the nucleotide sequence set forth in Seq. Id. No. 3.

2. An isolated RNA molecule that is complementary to the polynucleotide sequence of claim 1.

3. An expression vector comprising the polynucleotide sequence of claim 1.

* * * * *

SEQUENCE LISTING

<160> NUMBER OF SEQ ID NOS: 5

<210> SEQ ID NO 1
<211> LENGTH: 1233
<212> TYPE: DNA
<213> ORGANISM: Drosophila melanogaster

<400> SEQUENCE: 1

```
atggccgtgc ccttttattt gcccgagggc ggcgccgatg acgtagcgtc gagttcatcg      60
ggagcctcgg gcaactcctc cccccacaac cacccacttc cctcgagcgc atcctcgtcc     120
gtctcctcct cgggcgtgtc ctcggcctcc gcctcctcgg cctcatcttc gtcatccgca     180
tcgtcggacg gcgccagcag cgccgcctcg caatcgccga acaccaccac ctcgtcggcc     240
acgcagacgc cgatgcagtc tccactgccc accgaccaag tgctatacgc cctctacgag     300
tgggtcagga tgtaccagag ccagcagagt gccccgcaaa tcttccagta tccgccgcca     360
agcccctctt gcaatttcac tggcggcgat gtgttctttc cgcacggcca tccgaatccg     420
aactcgaatc cccatccgcg cacccccga accagcgtga gcttctcctc cggcgaggag     480
tacaacttct tccggcagca gcagccgcaa ccacatccgt catatccggc gccatcaaca     540
ccgcagccaa tgccaccgca gtcagcgccg ccgatgcact gcagccacag ctacccgcag     600
cagtcggcgc acatgatgcc acaccattcc gctcccttcg gaatgggcgg tacctactac     660
gccggctaca cgccaccacc cactccgaac acggccagtg cgggcacctc cagctcatcg     720
gcggccttcg gctggcacgg ccaccccac agcccttca cgtcgacctc cacgccgtta     780
tcggcgccag tggcgcccaa gatgcgcctg cagcgcagcc agtcggatgc ggccagacgc     840
aagcgattga cctcgacggg cgaggatgag cgcgagtacc agagcgatca tgaggccact     900
tgggacgagt ttggcgatcg ctacgacaac tttacggccg gcgggagcg tctgcaggag     960 ttcaatggac gcatcccgcc ccggaagaag aagagctcca atagccactc gagcagcagc    1020
```

-continued

| | |
|---|---|
| aataatccag tctgccatac cgacagccag tccggtggta catcccaagc ggagagcggt | 1080 |
| gccatccatg gccacatcag tcagcagcga caggtggagc gagaacgaca aaaggcgaag | 1140 |
| gccgagaaga agaaaccaca gagcttcact tggccaactg ttgtgaccgt tttcgttttg | 1200 |
| gccatgggct gtggcttctt tgcggcgcga tga | 1233 |

<210> SEQ ID NO 2
<211> LENGTH: 1233
<212> TYPE: DNA
<213> ORGANISM: Drosophila melanogaster

<400> SEQUENCE: 2

| | |
|---|---|
| atggccgtgc cctttattt gcccgagggc ggcgccgatg acgtagcgtc gagttcatcg | 60 |
| ggagcctcgg gcaactcctc cccccacaac cacccacttc cctcgagcgc atcctcgtcc | 120 |
| gtctcctcct cgggcgtgtc ctcggcctcc gcctcctcgg cctcatcttc gtcatccgca | 180 |
| tcgtcggacg gcgccagcag cgccgcctcg caatcgccga acaccaccac ctcgtcggcc | 240 |
| acgcagacgc cgatgcagtc tccactgccc accgaccaag tgctatacgc cctctacgag | 300 |
| tgggtcagga tgtaccagag ccagcagagt gccccgcaaa tcttccagta ccgccgcca | 360 |
| agccctctt gcaatttcac tggcggcgat gtgttctttc cgcacggcca tccgaatccg | 420 |
| aactcgaatc cccatccgcg ggcccccga accagcgtga gcttctcctc cggcgaggag | 480 |
| tacaacttct tccggcagca gcagccgcaa ccacatccgt catatccggc gccatcagca | 540 |
| ccgcagccaa tgccaccgca gtcagcgccg ccgatgcact gcagccacag ctacccgcag | 600 |
| cagtcggcgc acatgatgcc acaccattcc gctcccttcg gaatgggcgg tacctactac | 660 |
| gccggctaca cgccaccacc cactccgaac acggccagtg cgggcacctc cagctcatcg | 720 |
| gcggccttcg gctggcacgg ccaccccac gccccttca cgtcgacctc cacgccgtta | 780 |
| tcggcgccag tggcgcccaa gatgcgcctg cagcgcagcc agtcggatgc ggccagacgc | 840 |
| aagcgattga cctcgacggg cgaggatgag cgcgagtacc agagcgatca tgaggccact | 900 |
| tgggacgagt ttggcgatcg ctacgacaac tttacggccg ccgggagcg tctgcaggag | 960 |
| ttcaatggac gcatcccgcc ccggaagaag aagagctcca atagccactc gagcagcagc | 1020 |
| aataatccag tctgccatac cgacagccag tccggtggta catcccaagc ggagagcggt | 1080 |
| gccatccatg gccacatcag tcagcagcga caggtggagc gagaacgaca aaaggcgaag | 1140 |
| gccgagaaga agaaaccaca gagcttcact tggccaactg ttgtgaccgt tttcgttttg | 1200 |
| gccatgggct gtggcttctt tgcggcgcga tga | 1233 |

<210> SEQ ID NO 3
<211> LENGTH: 1233
<212> TYPE: DNA
<213> ORGANISM: Drosophila melanogaster

<400> SEQUENCE: 3

| | |
|---|---|
| atggccgtgc cctttattt gcccgagggc ggcgccgatg acgtagcgtc gagttcatcg | 60 |
| ggagcctcgg gcaactcctc cccccacaac cacccacttc cctcgagcgc atcctcgtcc | 120 |
| gtctcctcct cgggcgtgtc ctcggcctcc gcctcctcgg cctcatcttc gtcatccgca | 180 |
| tcgtcggacg gcgccagcag cgccgcctcg caatcgccga acaccaccac ctcgtcggcc | 240 |
| acgcagacgc cgatgcagtc tccactgccc accgaccaag tgctatacgc cctctacgag | 300 |
| tgggtcagga tgtaccagag ccagcagagt gccccgcaaa tcttccagta ccgccgcca | 360 |
| gccccctctt gcaatttcac tggcggcgat gtgttctttc gcacggcca tccgaatccg | 420 |

```
aactcgaatc cccatccgcg ggcccccga accagcgtga gcttctcctc cggcgaggag    480
tacaacttct tccggcagca gcagccgcaa ccacatccgt catatccggc gccatcagca    540
ccgcagccaa tgccaccgca gtcagcgccg ccgatgcact gcagccacag ctacccgcag    600
cagtcggcgc acatgatgcc acaccattcc gctcccttcg gaatgggcgg tacctactac    660
gccggctaca cgccaccacc cgctccgaac acggccagtg cgggcacctc cagctcatcg    720
gcggccttcg gctggcacgg ccaccccac gcccccttca cgtcgacctc cacgccgtta    780
tcggcgccag tggcgcccaa gatgcgcctg cagcgcagcc agtcggatgc ggccagacgc    840
aagcgattga cctcgacggg cgaggatgag cgcgagtacc agagcgatca tgaggccact    900
tgggacgagt ttggcgatcg ctacgacaac tttacggccg gccgggagcg tctgcaggag    960
ttcaatggac gcatcccgcc ccggaagaag aagagctcca atagccactc gagcagcagc   1020
aataatccag tctgccatac cgacagccag tccggtggta catcccaagc ggagagcggt   1080
gccatccatg gccacatcag tcagcagcga caggtggagc gagaacgaca aaaggcgaag   1140
gccgagaaga gaaaccaca gagcttcact tggccaactg ttgtgaccgt tttcgttttg   1200
gccatgggct gtggcttctt tgcggcgcga tga                               1233
```

<210> SEQ ID NO 4
<211> LENGTH: 410
<212> TYPE: PRT
<213> ORGANISM: Drosophila melanogaster

<400> SEQUENCE: 4

```
Met Ala Val Pro Phe Tyr Leu Pro Glu Gly Gly Ala Asp Asp Val Ala
 1               5                  10                  15

Ser Ser Ser Ser Gly Ala Ser Gly Asn Ser Ser Pro His Asn His Pro
                20                  25                  30

Leu Pro Ser Ser Ala Ser Ser Val Ser Ser Gly Val Ser Ser
            35                  40                  45

Ala Ser Ala Ser Ala Ser Ser Ser Ser Ala Ser Ser Asp Gly
    50                  55                  60

Ala Ser Ala Ala Ser Gln Ser Pro Asn Thr Thr Thr Ser Ser Ala
65                  70                  75                  80

Thr Gln Thr Pro Met Gln Ser Pro Leu Pro Thr Asp Gln Val Leu Tyr
                85                  90                  95

Ala Leu Tyr Glu Trp Val Arg Met Tyr Gln Ser Gln Gln Ser Ala Pro
               100                 105                 110

Gln Ile Phe Gln Tyr Pro Pro Pro Ser Pro Ser Cys Asn Phe Thr Gly
           115                 120                 125

Gly Asp Val Phe Phe Pro His Gly His Pro Asn Pro Asn Ser Asn Pro
       130                 135                 140

His Pro Arg Ala Pro Arg Thr Ser Val Ser Phe Ser Ser Gly Glu Glu
145                 150                 155                 160

Tyr Asn Phe Phe Arg Gln Gln Pro Gln Pro His Pro Ser Tyr Pro
               165                 170                 175

Ala Pro Ser Ala Pro Gln Pro Met Pro Pro Gln Ser Ala Pro Pro Met
           180                 185                 190

His Cys Ser His Ser Tyr Pro Gln Gln Ser Ala His Met Met Pro His
       195                 200                 205

His Ser Ala Pro Phe Gly Met Gly Gly Thr Tyr Tyr Ala Gly Tyr Thr
   210                 215                 220
```

```
Pro Pro Pro Thr Pro Asn Thr Ala Ser Ala Gly Thr Ser Ser Ser Ser
225                 230                 235                 240

Ala Ala Phe Gly Trp His Gly His Pro His Ala Pro Phe Thr Ser Thr
                245                 250                 255

Ser Thr Pro Leu Ser Ala Pro Val Ala Pro Lys Met Arg Leu Gln Arg
                260                 265                 270

Ser Gln Ser Asp Ala Ala Arg Arg Lys Arg Leu Thr Ser Thr Gly Glu
                275                 280                 285

Asp Glu Arg Glu Tyr Gln Ser Asp His Glu Ala Thr Trp Asp Glu Phe
                290                 295                 300

Gly Asp Arg Tyr Asp Asn Phe Thr Ala Gly Arg Glu Arg Leu Gln Glu
305                 310                 315                 320

Phe Asn Gly Arg Ile Pro Pro Arg Lys Lys Lys Ser Ser Asn Ser His
                325                 330                 335

Ser Ser Ser Ser Asn Asn Pro Val Cys His Thr Asp Ser Gln Ser Gly
                340                 345                 350

Gly Thr Ser Gln Ala Glu Ser Gly Ala Ile His Gly His Ile Ser Gln
                355                 360                 365

Gln Arg Gln Val Glu Arg Glu Arg Gln Lys Ala Lys Ala Glu Lys Lys
                370                 375                 380

Lys Pro Gln Ser Phe Thr Trp Pro Thr Val Val Thr Val Phe Val Leu
385                 390                 395                 400

Ala Met Gly Cys Gly Phe Phe Ala Ala Arg
                405                 410

<210> SEQ ID NO 5
<211> LENGTH: 410
<212> TYPE: PRT
<213> ORGANISM: Drosophila melanogaster

<400> SEQUENCE: 5

Met Ala Val Pro Phe Tyr Leu Pro Glu Gly Gly Ala Asp Asp Val Ala
1               5                   10                  15

Ser Ser Ser Ser Gly Ala Ser Gly Asn Ser Ser Pro His Asn His Pro
                20                  25                  30

Leu Pro Ser Ser Ala Ser Ser Ser Val Ser Ser Ser Gly Val Ser Ser
                35                  40                  45

Ala Ser Ala Ser Ser Ala Ser Ser Ser Ser Ala Ser Ser Asp Gly
    50                  55                  60

Ala Ser Ser Ala Ala Ser Gln Ser Pro Asn Thr Thr Ser Ser Ala
65                  70                  75                  80

Thr Gln Thr Pro Met Gln Ser Pro Leu Pro Thr Asp Gln Val Leu Tyr
                85                  90                  95

Ala Leu Tyr Glu Trp Val Arg Met Tyr Gln Ser Gln Gln Ser Ala Pro
                100                 105                 110

Gln Ile Phe Gln Tyr Pro Pro Ala Pro Ser Cys Asn Phe Thr Gly
                115                 120                 125

Gly Asp Val Phe Phe Pro His Gly His Pro Asn Pro Asn Ser Asn Pro
130                 135                 140

His Pro Arg Ala Pro Arg Thr Ser Val Ser Phe Ser Ser Gly Glu Glu
145                 150                 155                 160

Tyr Asn Phe Phe Arg Gln Gln Gln Pro Gln Pro His Pro Ser Tyr Pro
                165                 170                 175

Ala Pro Ser Ala Pro Gln Pro Met Pro Pro Gln Ser Ala Pro Pro Met
                180                 185                 190
```

-continued

```
His Cys Ser His Ser Tyr Pro Gln Gln Ser Ala His Met Met Pro His
        195                 200                 205
His Ser Ala Pro Phe Gly Met Gly Gly Thr Tyr Tyr Ala Gly Tyr Thr
    210                 215                 220
Pro Pro Pro Ala Pro Asn Thr Ala Ser Ala Gly Thr Ser Ser Ser Ser
225                 230                 235                 240
Ala Ala Phe Gly Trp His Gly His Pro His Ala Pro Phe Thr Ser Thr
                245                 250                 255
Ser Thr Pro Leu Ser Ala Pro Val Ala Pro Lys Met Arg Leu Gln Arg
            260                 265                 270
Ser Gln Ser Asp Ala Ala Arg Arg Lys Arg Leu Thr Ser Thr Gly Glu
        275                 280                 285
Asp Glu Arg Glu Tyr Gln Ser Asp His Glu Ala Thr Trp Asp Glu Phe
    290                 295                 300
Gly Asp Arg Tyr Asp Asn Phe Thr Ala Gly Arg Glu Arg Leu Gln Glu
305                 310                 315                 320
Phe Asn Gly Arg Ile Pro Pro Arg Lys Lys Lys Ser Ser Asn Ser His
                325                 330                 335
Ser Ser Ser Ser Asn Asn Pro Val Cys His Thr Asp Ser Gln Ser Gly
            340                 345                 350
Gly Thr Ser Gln Ala Glu Ser Gly Ala Ile His Gly His Ile Ser Gln
        355                 360                 365
Gln Arg Gln Val Glu Arg Glu Arg Gln Lys Ala Lys Ala Glu Lys Lys
        370                 375                 380
Lys Pro Gln Ser Phe Thr Trp Pro Thr Val Val Thr Val Phe Val Leu
385                 390                 395                 400
Ala Met Gly Cys Gly Phe Phe Ala Ala Arg
                405                 410
```